US010486712B2

(12) United States Patent
Niino et al.

(10) Patent No.: US 10,486,712 B2
(45) Date of Patent: Nov. 26, 2019

(54) EVACUATION CONTROL APPARATUS AND EVACUATION CONTROL METHOD

(71) Applicant: DENSO CORPORATION, Kariya, Aichi-pref. (JP)

(72) Inventors: Hiroaki Niino, Kariya (JP); Masao Ooka, Kariya (JP); Takeshi Miura, Kariya (JP); Hitoshi Wada, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 127 days.

(21) Appl. No.: 15/549,641

(22) PCT Filed: Feb. 2, 2016

(86) PCT No.: PCT/JP2016/053007

§ 371 (c)(1),
(2) Date: Aug. 8, 2017

(87) PCT Pub. No.: WO2016/129446

PCT Pub. Date: Aug. 18, 2016

(65) Prior Publication Data

US 2018/0029604 A1 Feb. 1, 2018

(30) Foreign Application Priority Data

Feb. 10, 2015 (JP) ................................. 2015-024524
Jan. 20, 2016 (JP) ................................. 2016-008948

(51) Int. Cl.
*A61B 5/18* (2006.01)
*B60W 50/00* (2006.01)
(Continued)

(52) U.S. Cl.
CPC ........... *B60W 50/0098* (2013.01); *A61B 5/18* (2013.01); *B60Q 1/52* (2013.01); *B60Q 1/525* (2013.01);
(Continued)

(58) Field of Classification Search
CPC ............................. B60W 50/0098; A61B 5/18
See application file for complete search history.

(56) References Cited

U.S. PATENT DOCUMENTS

2013/0314503 A1* 11/2013 Nix .................... G06K 9/00805 348/46
2015/0166062 A1* 6/2015 Johnson ................ B60W 30/12 701/41
(Continued)

FOREIGN PATENT DOCUMENTS

JP H10-293899 A 11/1998
JP 2003-118424 A 4/2003
(Continued)

*Primary Examiner* — Jess Whittington
(74) *Attorney, Agent, or Firm* — Knobbe, Martens, Olson & Bear, LLP

(57) ABSTRACT

An evacuation control apparatus includes a decrease detecting unit, a rear monitoring unit, and an evacuation control unit. The decrease detecting unit detects decrease in a consciousness level of a driver of an own vehicle. The rear monitoring unit monitors a state behind the own vehicle. The evacuation control unit outputs control information for making the own vehicle perform an emergency evacuation based on monitoring results of the rear monitoring unit, when the decrease detecting unit detects decrease in the consciousness level of the driver.

17 Claims, 10 Drawing Sheets

(51) Int. Cl.

| | |
|---|---|
| ***B60R 21/00*** | (2006.01) |
| ***G01C 21/26*** | (2006.01) |
| ***B60W 50/14*** | (2012.01) |
| ***B60Q 1/52*** | (2006.01) |
| ***B60W 10/00*** | (2006.01) |
| ***B60W 30/00*** | (2006.01) |
| ***G08G 1/0962*** | (2006.01) |
| ***G08G 1/16*** | (2006.01) |
| ***G06K 9/00*** | (2006.01) |
| ***B60W 10/18*** | (2012.01) |
| ***B60W 10/20*** | (2006.01) |
| ***B60W 30/18*** | (2012.01) |
| ***G08G 1/052*** | (2006.01) |
| ***G08G 1/0968*** | (2006.01) |
| ***G05D 1/00*** | (2006.01) |
| *G08G 1/017* | (2006.01) |
| *G08G 1/04* | (2006.01) |

(52) U.S. Cl.

CPC ............. *B60R 21/00* (2013.01); *B60W 10/00* (2013.01); *B60W 10/18* (2013.01); *B60W 10/20* (2013.01); *B60W 30/00* (2013.01); *B60W 30/18163* (2013.01); *B60W 50/14* (2013.01); *G01C 21/26* (2013.01); *G05D 1/0061* (2013.01); *G06K 9/00845* (2013.01); *G08G 1/052* (2013.01); *G08G 1/09626* (2013.01); *G08G 1/096827* (2013.01); *G08G 1/096833* (2013.01); *G08G 1/162* (2013.01); *G08G 1/166* (2013.01); *G08G 1/167* (2013.01); *B60K 2370/169* (2019.05); *B60W 2050/146* (2013.01); *B60W 2420/42* (2013.01); *B60W 2420/52* (2013.01); *B60W 2510/24* (2013.01); *B60W 2510/244* (2013.01); *B60W 2540/26* (2013.01); *B60W 2550/00* (2013.01); *B60W 2550/12* (2013.01); *G05D 2201/0213* (2013.01); *G08G 1/0175* (2013.01); *G08G 1/04* (2013.01)

(56) References Cited

U.S. PATENT DOCUMENTS

| | | | | |
|---|---|---|---|---|
| 2015/0363986 | A1* | 12/2015 | Hoyos .................. | H05K 999/99 340/5.61 |
| 2016/0071418 | A1* | 3/2016 | Oshida ..................... | G08G 1/22 701/23 |
| 2017/0355377 | A1* | 12/2017 | Vijaya ................... | B60W 40/08 |

FOREIGN PATENT DOCUMENTS

| | | | |
|---|---|---|---|
| JP | 2008-037218 | A | 2/2008 |
| JP | 2009-163434 | A | 7/2009 |
| JP | 2011-189776 | A | 9/2011 |
| JP | 2013-109446 | A | 6/2013 |
| JP | 2014-075008 | A | 4/2014 |

* cited by examiner 1
6A
6B
6
FRONT MONITOR SENSOR
16
ROUTE CALCULATING UNIT
19
PASSENGER DETECTING UNIT
8
10
NAVIGATION SYSTEM
4A
4B
4
REAR MONITOR SENSOR
18
EVACUATION CONTROL UNIT
14
CONFIRMING UNIT
IN-VEHICLE LAN
12
VEHICLE CONTROL ECU
2
DRIVER STATE SENSOR
11
CONSCIOUSNESS LEVEL DETERMINING UNIT
13
WARNING UNIT

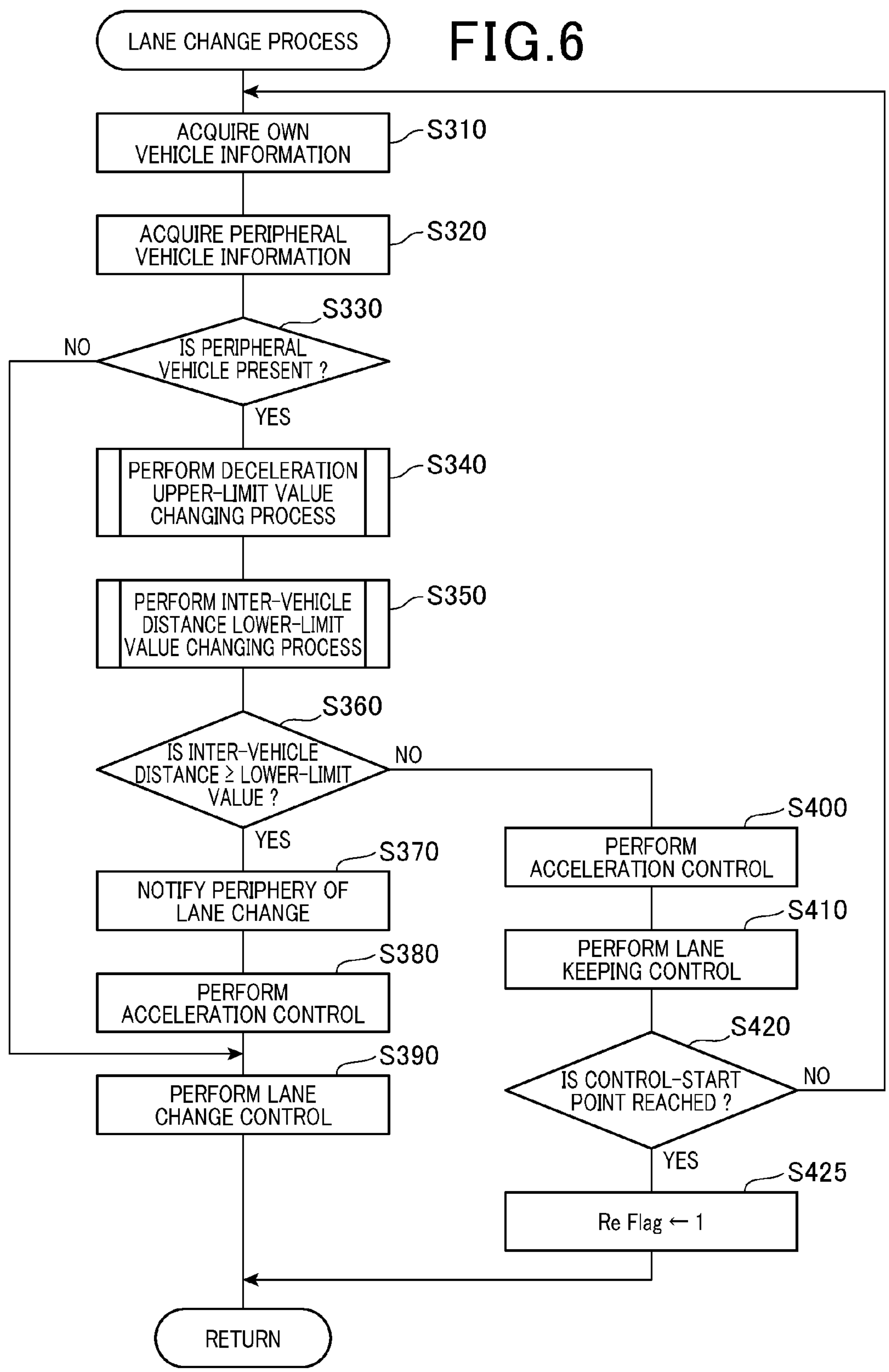
FIG.6
LANE CHANGE PROCESS
ACQUIRE OWN VEHICLE INFORMATION
S310
ACQUIRE PERIPHERAL VEHICLE INFORMATION
S320
S330
IS PERIPHERAL VEHICLE PRESENT ?
NO
YES
PERFORM DECELERATION UPPER-LIMIT VALUE CHANGING PROCESS
S340
PERFORM INTER-VEHICLE DISTANCE LOWER-LIMIT VALUE CHANGING PROCESS
S350
S360
IS INTER-VEHICLE DISTANCE ≥ LOWER-LIMIT VALUE ?
NO
YES
S370
NOTIFY PERIPHERY OF LANE CHANGE
S380
PERFORM ACCELERATION CONTROL
S390
PERFORM LANE CHANGE CONTROL
S400
PERFORM ACCELERATION CONTROL
S410
PERFORM LANE KEEPING CONTROL
S420
IS CONTROL-START POINT REACHED ?
NO
YES
S425
Re Flag ← 1
RETURN

EVACUATION CONTROL APPARATUS AND EVACUATION CONTROL METHOD

CROSS-REFERENCE TO RELATED APPLICATIONS

The present application is based on and claims the benefit of priority from Japanese Patent Application No. 2015-024524, filed on Feb. 10, 2015, and Japanese Patent Application No. 2016-008948, filed on Jan. 20, 2016, the descriptions of which are incorporated herein by reference.

TECHNICAL FIELD

The present disclosure relates to a technology for detecting decrease in the consciousness level of a driver of an own vehicle and evacuating the own vehicle.

BACKGROUND ART

Conventionally, a following technology is known for when the consciousness level of a driver who is driving a vehicle decreases, such as when the driver experiences strong drowsiness or loses consciousness, and problems with driving occur. In this technology, to ensure the safety of the own vehicle and other vehicles, the own vehicle is evacuated to an evacuation area, such as a road-shoulder area, by traveling assistance control and stopped.

For example, in PTL 1, a following technology is proposed for when the consciousness level of a driver decreases. In this technology, in addition to road-shoulder areas, stop lines, intersections, and the like are selected as appropriate as the evacuation area of the own vehicle. A target stop position is determined to make the own vehicle perform an emergency evacuation to these evacuation areas. Deceleration and the like of the own vehicle are determined so that the own vehicle stops at the target stop position.

CITATION LIST

Patent Literature

[PTL 1] JP-A-2009-163434

SUMMARY OF INVENTION

Technical Problem

However, as a result of thorough examination by the inventors, an issue has been found in that, in the conventional technology, excessive inconvenience may be inflicted on rear vehicles, such as a driver of a rear vehicle experiencing impact, contact, or a risk thereof as a result of sudden deceleration, course change, or the like of the own vehicle during emergency evacuation.

An object of the present disclosure is to provide a technology that enables both care for a rear vehicle and promptness of evacuation to be more favorably achieved when an own vehicle must perform an emergency evacuation.

An evacuation control apparatus according to an aspect of the present disclosure includes a decrease detecting unit, a rear monitoring unit, and an evacuation control unit. The decrease detecting unit detects decrease in a consciousness level of a driver of an own vehicle. The rear monitoring unit monitors a state behind the own vehicle. The evacuation control unit outputs control information for making the own vehicle perform an emergency evacuation based on monitoring results from the rear monitor, when the decrease detecting unit detects decrease in the consciousness level of the driver.

As a result of a configuration such as this, when the own vehicle is to perform an emergency evacuation, traveling assistance control that takes into consideration the rear monitoring results can be performed. Therefore, deceleration, course change, and the like based on the state behind the own vehicle can be performed. Furthermore, both care for a rear vehicle and promptness of evacuation can be further achieved.

In addition, in the evacuation control apparatus according to an aspect of the present disclosure, a warning unit and a confirming unit may be further included. The warning unit issues a warning towards the rear of the own vehicle when the decrease detecting unit detects decrease in the consciousness level of the driver. The confirming unit confirms whether or not the warning by the warning unit is successful. The evacuation control unit outputs the control information for making the own vehicle perform an emergency evacuation based on confirmation results from the confirming unit.

As a result of a configuration such as this, when the own vehicle is to perform an emergency evacuation, traveling assistance control that takes into consideration the warning confirmation results can be performed. Therefore, deceleration, course change, and the like based on whether or not the warning to the rear of the own vehicle is successful can be performed. Furthermore, both care for a following vehicle and promptness of evacuation can be further achieved.

In addition, an evacuation control method according to an aspect of the present disclosure detects, by an evacuation control apparatus mounted in an own vehicle, decrease in a consciousness level that is an indicator indicating a state of awareness of a driver of the own vehicle, issues a warning to the rear of the own vehicle when the decrease in the consciousness level of the driver is detected, confirms whether or not the warning is successful, and outputs control information for making the own vehicle perform an emergency evacuation based on confirmation results related to the warning. As a result of this configuration, similar effects can be achieved due to reasons similar to those of the above-described evacuation control apparatus.

Reference numbers within the parentheses in the scope of claims indicate corresponding relationships with specific means according to an embodiment described hereafter as an aspect, and do not limit the technical scope of the present invention.

BRIEF DESCRIPTION OF DRAWINGS

FIG. 6 is a flowchart of a lane change process;

DESCRIPTION OF EMBODIMENTS

An embodiment to which the present disclosure is applied will hereinafter be described with reference to the drawings.

[1. First Embodiment]

[1-1. Configuration]

Figure 1:
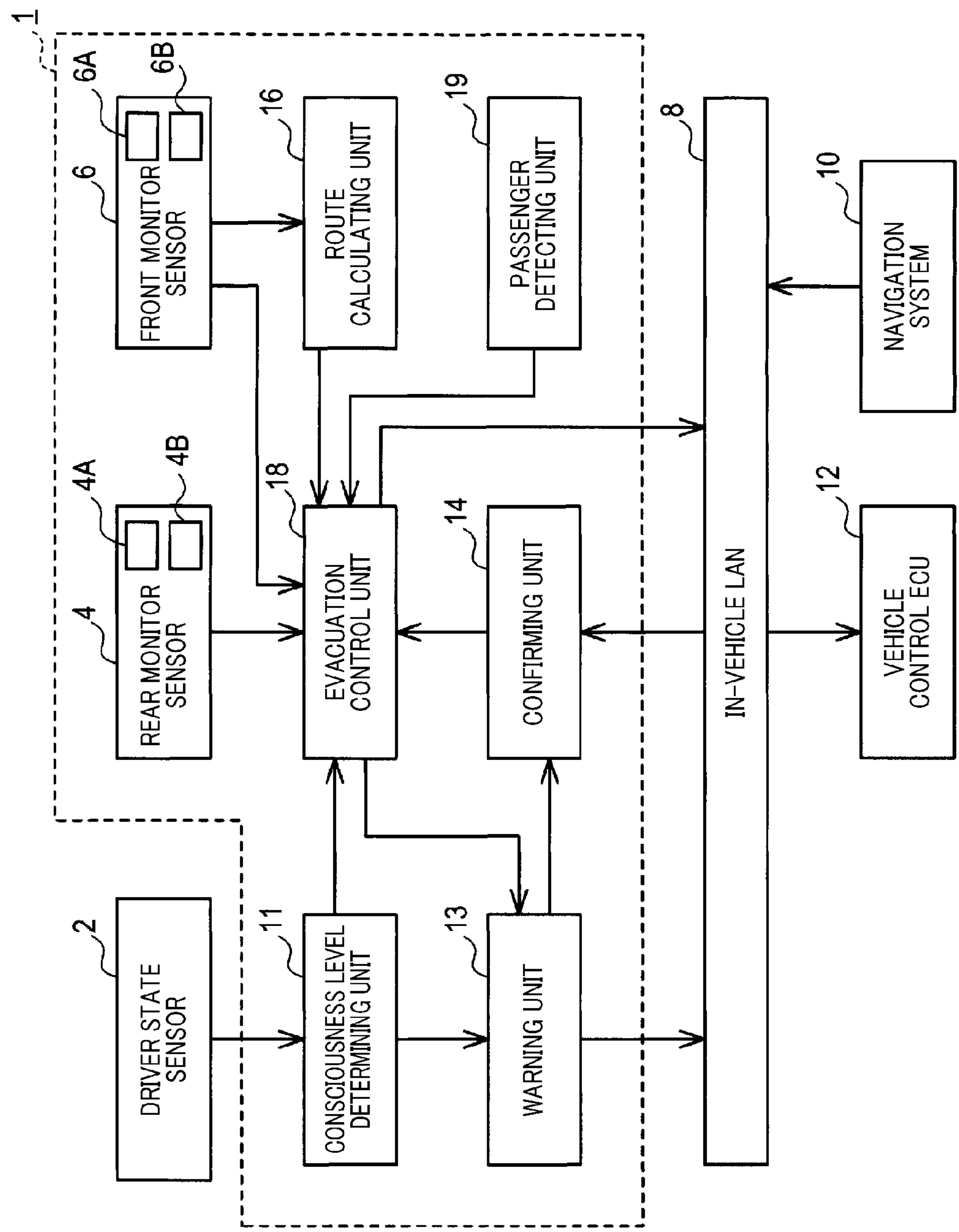
FIG. 1 is a block diagram of a configuration of an evacuation control apparatus according to an embodiment.

An evacuation control apparatus 1 shown in FIG. 1 is mounted in a vehicle. The evacuation control apparatus 1 is connected to each of a driver state sensor 2 and an in-vehicle local area network (hereafter, an in-vehicle LAN) 8. The evacuation control apparatus 1 includes a rear monitor sensor 4, a front monitor sensor 6, a consciousness level determining unit 11, a warning unit 13, a confirming unit 14, a route calculating unit 16, an evacuation control unit 18, and a passenger detecting unit 19. Hereafter, the vehicle in which these constituent elements are mounted is referred to as an own vehicle.

In addition, the evacuation control apparatus 1 includes an electronic control unit (ECU). The ECU is mainly configured by a microcomputer and a communication controller for the in-vehicle LAN. The microcomputer included in the ECU has a central processing unit (CPU), a random access memory (RAM), a read-only memory (ROM), and a non-transitory, tangible recording medium (hereafter, a memory) that is typically a semiconductor memory, such as a flash memory.

The evacuation control apparatus 1 is such that, in the microcomputer in the ECU, the CPU performs various processes based on programs stored in the memory. That is, a method corresponding to a program is performed as a result of the CPU running the program. The number of microcomputers may be a single or a plurality of microcomputers. An installation area of the single or plurality of microcomputers may be any area inside the vehicle.

In addition, the warning unit 13, the confirming unit 14, the route calculating unit 16, and the evacuation control unit 18 of the evacuation control apparatus 1 are configurations of functions actualized by the CPU performing various processes in the microcomputer in the ECU. Some or all of these functions provided by the microcomputer of the evacuation control apparatus 1 may be configured by hardware by a single or a plurality of logic circuits or electronic circuits, such as integrated circuits (ICs). That is, in the ECU of the evacuation control apparatus 1, the above-described functions can be provided, not only by software, but by hardware or a combination of software and hardware.

The in-vehicle LAN 8 is a local area network that is provided inside the own vehicle. For example, the in-vehicle LAN 8 transmits various types of information using a known communication protocol, such as Controller Area Network (CAN), FlexRay, Local Interconnect Network (LIN), Media Oriented Systems Transport (MOST), or Audio Visual Communication-Local Area Network (AVC-LAN). In addition to the ECU of the evacuation control apparatus 1, various ECUs including an ECU of a navigation system 10 and a vehicle control ECU 12 are each connected to the in-vehicle LAN 8. These ECUs that are connected to the in-vehicle LAN 8 are configured to share vehicle information, such as detection information of various sensors and control information within the ECU.

The driver state sensor 2 is mounted in the own vehicle. The driver state sensor 2 is configured by a single or a plurality of sensors and the like that detect the state of the driver of the own vehicle by a publicly known method. For example, a driver status monitor, a biological sensor, a microphone, and switches may be example of the sensor. The state of the driver herein is merely required to be information that enables general classification into a state in which driving operation of the vehicle can be safely performed and a state in which driving operation of the vehicle cannot be safely performed. The state of the driver is detected by the driver state sensor 2, such as the driver status monitor, the biological sensor, the microphone, and the switches.

For example, the driver status monitor is set in a lower portion of a meter hood inside the vehicle cabin. The driver status monitor is configured by a near-infrared camera, an ECU, an audio output apparatus (such as a speaker), and the like. Of the foregoing, the near-infrared camera captures an image of a face portion of the driver. The ECU analyzes an orientation of the face of the driver, opening of the eyes, and the like based on the image (hereafter, a facial image) including the face portion of the driver that has been captured by the near-infrared camera. For example, when determined that a state in which the driver has their eyes closed or is not facing forward has continued for a determined amount of time, the ECU performs a process such as issuing a warning to the driver via the audio output apparatus or the like and thereby prompting safe driving. That is, various states related to the actions of the driver can be detected by the driver status monitor.

In addition, for example, the biological sensor is capable of detecting various states related to the biological body of the driver, such as body temperature, blood-pressure value, heart rate, and respiratory rate. Furthermore, for example, a pressing switch for emergencies, a microphone of the audio output apparatus, and the like can detect an impaired condition and the like of the driver through direct input by the driver themselves or a passenger. Information detected by the driver state sensor 2 such as this is outputted to the consciousness level determining unit 11 at every predetermined cycle.

The consciousness level determining unit 11 determines whether or not the consciousness level of the driver is equal to or lower than a predetermined value (such as a predetermined threshold), based on the detection information from the driver state sensor 2. As a result, when decrease in the consciousness level of the driver is detected, the consciousness level determining unit 11 notifies the warning unit 13 and the evacuation control unit 18 of the decrease. The consciousness level is an indicator that indicates a state of awareness of the driver. Regarding the consciousness level, the degree of awareness of the driver increases as the value of the consciousness level increases. The degree of awareness of the driver decreases as the value of the consciousness level decreases. In addition, the consciousness level is also information that indicates the degree to which the state of the driver is the state in which driving operation of the vehicle can be safely performed.

Specifically, for example, the consciousness level can be calculated by the amount of time over which the driver is continuously closing their eyes, the amount of time over Which the movement of the driver is continuously undetected, and numeric values of the body temperature, blood-pressure value, heart rate, respiratory rate, and the like of the driver respectively being weighted and then calculated. The calculated consciousness level can then be stored in the memory. As a result of threshold determination being performed on the consciousness level, decrease in the consciousness level of the driver can be detected.

When input by the pressing switch for emergencies and the like is performed, a determination may be made that the consciousness level of the driver is at the lowest. For example, when decrease in the consciousness level of the driver is detected, the driver may be requested to determine whether or not to make the own vehicle perform an emergency stop, via the speaker, a display, or the like. Subsequently, when the switch input or the like is performed, it may be considered that the consciousness level of the driver is at the lowest. In addition, the consciousness level determining unit 11 may calculate the consciousness level of the driver and detect the decrease in the consciousness level of the driver. When determined that the consciousness level of the driver is at the lowest, the consciousness level determining unit 11 may notify the warning unit 13 and the evacuation control unit 18. That is, when a determination is made that the consciousness level of the driver is at the lowest, an evacuation control process, described hereafter, can also be started. According to the present embodiment, the consciousness level determining unit 11 corresponds to a decrease detecting unit.

Upon receiving the detection information from the consciousness level determining unit 11, the warning unit 13 issues a warning to the rear of the own vehicle, ahead of the own vehicle, or to the periphery of the own vehicle including at least either of the rear of and ahead of the own vehicle. A method for warning includes a method in which notification of an emergency state of the own vehicle is given using various communication means, such as inter-vehicle communication and road-vehicle communication, a method in which notification of an emergency state of the own vehicle is given by hazard lights or a horn being operating in, for example, a mode differing from normal mode or in the normal mode, and the like. In addition, brake lamps can be used to issue a warning to the rear of the own vehicle, and headlights can be used to issue a warning ahead of the own vehicle (such as passing). Of these methods, for example, when the communication means is used, various types of information can be included in a. transmission signal.

Figure 2:
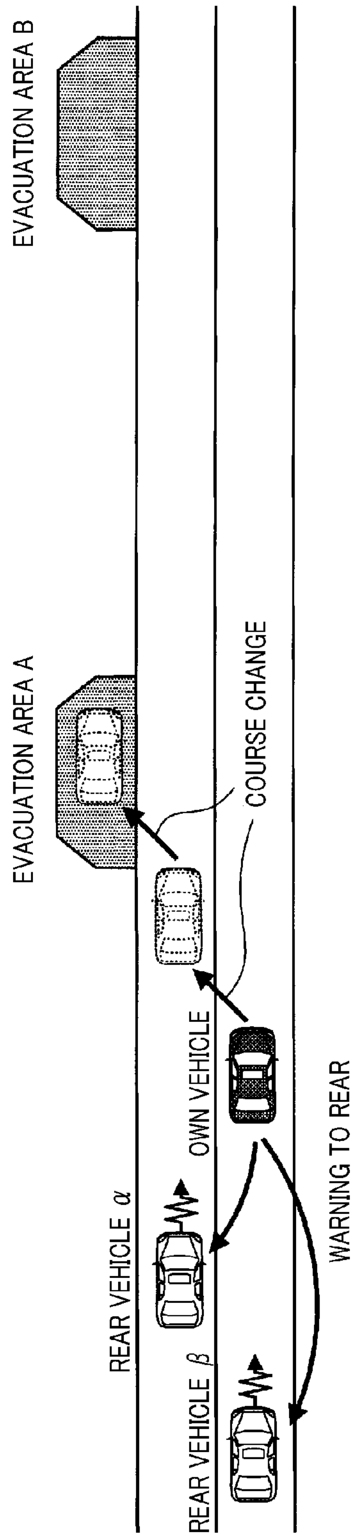
FIG. 2 is a diagram of an example of a hypothetical positional relationship among an own vehicle, rear vehicles, and evacuation areas, and a progression by which the own vehicle performs an emergency evacuation to an evacuation area.

For example, the information included in the transmission signal includes information indicating that the consciousness level of the driver has decreased, information identifying the own vehicle by a license plate or the like, and information notifying a driver of a vehicle that has received the transmission signal of these pieces of information and requesting transmission of a response signal (hereafter, ACK). Information identifying the other vehicle (such as a rear vehicle shown in FIG. 2) that has received the transmission signal by a license plate or the like can be included in the ACK.

Under the premise of these methods, the warning unit 13 issues a request to the vehicle control ECU 12 via the in-vehicle LAN 8 to illuminate the lights, operate the horn, or the like, a request to a short-range wireless apparatus (not shown) to broadcast the transmission signal, and the like. In addition, the warning unit 13 notifies the confirming unit 14 that such requests have been made.

The confirming unit 14 confirms whether or not the warning by the warning unit 13 is successful. A method for this confirmation includes a method in which confirmation is made by, for example, information indicating the illumination or flashing of the hazard lights, brake lamps, and headlights, and operation of the horn, or notification that the transmission signal has been broadcast being received from the in-vehicle LAN 8 within a predetermined amount of time from reception of the notification from the warning unit 13. When the success of the warning is confirmed by these methods, the confirming unit 14 stores a success level 1 flag in the memory. The success level 1 flag indicates that success at a first level has been confirmed.

In addition, for example, as the above-described method for confirmation, there is a method in which, after the success at the first level, confirmation is made by the ACK in response to the transmission signal being received from a rear vehicle, a vehicle ahead, or a vehicle (hereafter, a peripheral vehicle) in the periphery of the own vehicle including at least either of the rear vehicle and the vehicle ahead, or a change in behavior of a peripheral vehicle being detected. For example, when the ACK is received from a peripheral vehicle, the rear vehicle or the vehicle ahead that has received the transmission signal can be identified as a result of the license plate of the rear vehicle or the vehicle ahead being recognized from a captured image of a rear monitor camera 4A or a front monitor camera 6A. In addition, changes in the behaviors of the peripheral vehicles can be detected as a result of deceleration of a rear vehicle, acceleration of a vehicle ahead, increase in inter-vehicle distance to a peripheral vehicle, passing by a rear vehicle, operation of a horn or hazard lights of a peripheral vehicle, and the like being recognized.

When a response from a peripheral vehicle in relation to the warning is detected in this way, the confirming unit 14 stores a success level 2 flag in the memory, in place of the success level 1 flag. The success level 2 flag indicates that success at a second level has been confirmed. The behavior of a peripheral vehicle refers to action related to traveling of the peripheral vehicle. The behavior of a peripheral vehicle includes, not only visual action such as movement of the peripheral vehicle that can be recognized by a camera or the like, but also auditory action such as the horn of the peripheral vehicle or the like that can be recognized by a microphone or the like.

Information that has been confirmed by the confirming unit 14 in this way is outputted to the evacuation control unit 18. For example, the information includes information indicating whether or not the warning is successful, information indicating the success level when the warning is successful, and information indicating the peripheral vehicle identified when the warning is successful. Of the peripheral vehicles, the rear vehicle refers to another vehicle present behind the own vehicle, and the vehicle ahead refers to another vehicle present ahead of the own vehicle. In addition, hereafter, regarding other vehicles traveling in the same advancing direction as the own vehicle, of the rear vehicles, a vehicle traveling in the same traffic lane (that is, an own lane) as the own vehicle is referred to as a following vehicle. Of the peripheral vehicles, a vehicle traveling in a traffic lane (that is, an adjacent lane) on the side to which the own vehicle is to change traffic lanes is referred to as a side vehicle. For example, in FIG. 2, a rear vehicle $\alpha$ that is traveling in the adjacent lane corresponds to the side vehicle and a rear vehicle $\beta$ that is traveling in the own lane corresponds to the following vehicle.

The rear monitor sensor 4 is a sensor that monitors the state behind the own vehicle. For example, the rear monitor camera 4A and a rear monitor radar 4B are used in the sensor.

The front monitor sensor 6 is a sensor that monitors the state ahead of the own vehicle. For example, the front monitor camera 6A and a front monitor radar 6B are used in the sensor. In addition to these sensors, side monitor sensors that monitor the state on both sides of the own vehicle may be further provided. Regarding the configuration of the side monitor sensor, a configuration that is identical to the configurations of the rear monitor sensor 4 and the front monitor sensor 6, or a configuration based on these configurations can be used.

For example, the rear monitor camera 4A and the front monitor camera 6A each have a known image sensor, such as a complementary metal-oxide-semiconductor (CMOS) or a charge-coupled device (CCD). The rear monitor camera 4A and the front monitor camera 6A respectively have optical axes that are slightly downward relative to the horizontal towards the rear of the vehicle and ahead of the vehicle, and capture images of areas that spread over a predetermined angular range. Incident light from behind the vehicle and ahead of the vehicle is subjected to photoelectric conversion by the image sensor. Signals read out as voltages of accumulated charge are amplified, and then converted to digital images (that is, a rear image and a front image) of a predetermined luminance gradation by analog-to-digital (A/D) conversion.

The rear monitor camera 4A and the front monitor camera. 6A detect the shapes of vehicles from the rear image and the front image by a known method. For example, the detection is performed by a matching process using object models that are registered in advance. The object models are prepared for each type of object, such as a vehicle, a pedestrian, and a bicycle, and each feature of the object, such as a standard-sized car, a large vehicle, and a compact car. Therefore, the type and features of an object can be identified by the object models. In addition, more specific features of an object, such as shape, color, and luminance can also be identified.

Based on a position in an upward/downward direction of a peripheral vehicle and a position of a point at infinity (that is, FOE) in an image detected in the foregoing manner, a lateral-coordinate position (that is, a lateral position) and a vertical-coordinate position (that is, a vertical position) of the peripheral vehicle on a two-dimensional plate is detected. The two-dimensional plane is that in which, regarding a road surface in actual space, a vehicle width direction of the own vehicle is the lateral coordinate and a vehicle length direction of the own vehicle is the vertical coordinate. However, in the rear monitor camera 4A and the front monitor camera 6A, detection accuracy of relative distance decreases when a lower end position of the peripheral vehicle in the image is not accurately detected. Therefore, the rear monitor camera 4A and the front monitor camera 6A have a characteristic in that detection error related to the distance of the peripheral vehicle becomes relatively large. The rear monitor radar 4B and the front monitor radar 6B can be used to supplement such detection errors.

The rear monitor radar 4B and the front monitor radar 6B transmit radar waves, typically millimeter waves, laser light, ultrasonic waves, or the like, and calculate a distance to an object based on the amount of time until a reflected wave of the transmitted radar wave reflected by the object is received. An orientation (that is, an angle) of the object in relation to the own vehicle is determined by a reception direction of the reflected waves. Therefore, the position of the object or, specifically, the relative position in relation to the own vehicle can be identified by the calculated distance and angle.

For example, in a millimeter wave radar, transmission waves that have been frequency-modulated by triangular waves are outputted from an antenna. The reflected waves reflected from another vehicle (that is, a peripheral vehicle) present in the periphery of the own vehicle are received by the antenna and mixed. A beat signal is thereby acquired. The waveform of the beat signal changes as a result of interference generated based on the distance to the peripheral vehicle and the relative speed. Therefore, the relative distance and the relative speed are calculated from such a waveform. In addition, the reflected waves are received when a peripheral vehicle is present in the irradiation direction of the transmission waves. Therefore, the direction of another vehicle (that is, a peripheral vehicle) present in the periphery of the own vehicle can be detected. However, in the rear monitor radar 4B and the front monitor radar 6B, the reception direction of the reflected waves differs depending on the section of the body of the peripheral vehicle that reflects the radar waves, such as the millimeter waves. Therefore, the rear monitor radar 4B and the front monitor radar 6B have a characteristic in that detection error related to the direction of the peripheral vehicle is relatively large. The rear monitor camera 4A and the front monitor camera 6A can conversely supplement such detection errors.

In the rear monitor sensor 4 and the front monitor sensor 6, as a result of peripheral vehicles being identified by the rear monitor camera 4A and the front monitor camera 6A, and the relative positions of the identified peripheral vehicles being tracked, the advancing direction of each peripheral vehicle can be identified. In addition, a traveling lane (that is, the own lane) of the own vehicle can be identified using a method such as white line detection, described hereafter, and a following vehicle and a side vehicle can be distinguished by a relationship between the peripheral vehicle and the traffic lane, such whether each peripheral vehicle is a following vehicle (such as the rear vehicle β shown in FIG. 2) traveling in the own lane, a side vehicle (such as the rear vehicle α shown in FIG. 2) traveling in an adjacent lane on a road-shoulder side, and the like. Distinguishing information of the peripheral vehicles identified by the rear monitor sensor 4 and the front monitor sensor 6 in this way, distance information, and speed information are outputted to the evacuation control unit 18. According to the present embodiment, the rear monitor sensor 4 corresponds to a rear monitoring unit and the front monitor sensor 6 corresponds to a front monitoring unit.

The navigation system 10 acquires positional information of the own vehicle using an arrival time of radio waves received from a global positioning system (GPS) satellite. In addition, the navigation system 10 has a map database (hereafter, a map DB) that includes road map information associated with positional information such as longitudes and latitudes. The road map information is a database in the form of a table that associates link information of links configuring roads and node information of nodes connecting links to links. The link information includes link lengths, road widths, connection nodes, curve information and the like. Therefore, a road shape can be detected using the road map information. In addition, the map DB stores therein additional information including road type, such as automobile-only road, expressway, and local road, the number of traveling lanes, evacuation areas where a vehicle can make an emergency stop, and the like.

The navigation system 10 extracts the road map information from the map DB based. on a current position and generates graphic information based on the road map information. The navigation system 10 then displays, on a display, the graphic information on which a mark indicating the own vehicle position, icons indicating various facilities and registered names, and the like are superimposed. In addition, when a destination is inputted from an operating unit, the navigation system 10 retrieves a route from the current location to the destination. The navigation system 10 then guides the occupant to the destination by highlighting the route in the graphic information, generating audio information that is outputted from the speaker before left and right turns, and the like.

The navigation system 10 accumulates traveling direction detected by a gyro sensor and traveling distance detected by a vehicle speed sensor in the position information detected by the GPS, and detects the current position of the own vehicle with high accuracy. Therefore, for example, the distance from the position of the own vehicle on a link to a node, such as an evacuation area ahead, can be detected. In addition, for example, when the own vehicle is traveling on a road that has a plurality of traveling lanes in the same advancing direction, the traveling lane (that is, the own lane) in which the own vehicle is positioned can be detected. Navigation information indicating the own lane and the position of the own vehicle, the position of an evacuation area, the distance to the evacuation area, and the liked that are detected by the navigation system 10 in this manner is outputted to the route calculating unit 16.

In addition, the rear monitor camera 4A and the front monitor camera 6A detect lane boundary lines of a traffic lane (that is, the own lane) in which the own vehicle is traveling, an adjacent traffic lane, and the like from the captured rear image and front image. Specifically, for example, based on luminance in image data, a search for an area having luminance that is equal to or greater than a predetermined threshold is conducted in an upward direction from a bottom portion of a frame. An edge is thereby detected. A white line has edges composed of high-frequency components on both ends. Therefore, when differentiation of the luminance values in the image data is performed in a horizontal direction, peaks are obtained on both ends of the white line. Pixels of which a gradient or difference in luminance in the horizontal direction is equal to or greater than a predetermined value is an edge.

A white line portion can be estimated by the edges being connected in an upward/downward direction of the front image. As a result of a technique such as matching being applied to the estimated white line portion based on features such as a threshold of a white line width and a. linear shape, the white line is detected. Lane boundary lines of other colors, such as yellow lines and blue lines, can be determined by a method similar to that for the white line by, for example, weighting of the luminance in the image data being variably set for each pixel color, such as red, green, and blue (RGB).

As a result of a plurality of edges included in the lane boundary line, such as the white line, determined in this manner being extracted and, for example, subjected to a Hough transform, a model formula of the lane boundary line in each traffic lane is obtained. The model formula indicates the positions of the respective left and right lane boundary lines in relation to each traffic lane. A coefficient of the model formula also includes information such as a vanishing point of each left and right lane boundary line, a road curvature, a yaw angle, a road width, and an offset amount. Traffic lane information indicating the model formula of each traffic lane acquired by the front monitor camera 6A in this manner is outputted to the route calculating unit 16.

The route calculating unit 16 corrects the navigation information received from the navigation system 10 based on the traffic lane information received from the rear monitor camera 4A and the front monitor camera CA. The route calculating unit 16 then calculates a target traveling route from the own vehicle to an evacuation area, based on the corrected own lane and own vehicle position, the position of the evacuation area, and the distance to the evacuation area. A shape of an evacuation area is identified based on a shape of a traffic lane boundary line closest to the road shoulder. Of the evacuation area of which the shape is identified, a position farthest from the own vehicle is detected as a longest evacuation position.

A distance along the target traveling route to the detected longest evacuation position is calculated as a longest evacuation distance. Evacuation target information indicating the distance to the evacuation area, the shape of the evacuation area, the target traveling route, the longest evacuation distance, and the like, calculated by the route calculating unit 16 in this manner is outputted to the evacuation control unit 18.

The vehicle control ECU 12 is a single or a plurality of ECUs that perform various types of control related to the own vehicle. According to the present embodiment, in addition to control related to the illumination of lights, the operation of a horn, and the short-range wireless apparatus, described above, the vehicle control ECU 12 perform known traveling assistance control related to the own vehicle. In the traveling assistance control, automatic traveling of the own vehicle can be performed by control commands being transmitted to a throttle ACT, a brake ACT, a steering ACT, and the like. ACT is an abbreviation for actuator. For example, when control information including a course-change timing command is received from the evacuation control unit 18, the vehicle control ECU 12 transmits a control command to the ACTs including the steering ACT at a timing based on the received command. As a result, for example, the course of the own vehicle can be changed to enable the own vehicle to change traffic lanes to an adjacent lane on a road-shoulder side, to move to a road-shoulder area, and the like.

In addition, when control information including an evacuation command is received from the evacuation control unit 18, the vehicle control ECU 12 transmits a control command to the ACTs including the throttle ACT and the brake ACT such that the own vehicle stops at a target stop position along the target traveling route based on the received command. As a result, the own vehicle is made to perform an emergency evacuation to an evacuation area including a road-shoulder area.

In the vehicle control ECU 21, when course change or stop control of the own vehicle is performed, for example, an obstacle is detected by the front monitor camera 6A and the like, and traveling assistance control is performed so that the own vehicle does not collide or come into contact with the detected obstacle and the like. In addition, as the above-described traveling assistance control, for example, the vehicle control ECU 12 is configured to be capable of performing vehicle control to actualize functions of adaptive cruise control (hereafter, ACC), and lane keeping assist (hereafter, LKA). These functions are known technology. Therefore, descriptions thereof are omitted.

The passenger detecting unit 19 detects whether or not a passenger is present in the own vehicle. A passenger refers to an occupant in the own vehicle other than the driver.

For example, whether or not a passenger is present may be detected by a weight sensor or an in-cabin camera. Alternatively, whether or not a passenger is present may be detected by wireless communication with a mobile terminal carried by the passenger, various types of switch operation, and the like. In addition, when a passenger is present in the own vehicle, the type of passenger may be recognized. As the type of passenger, for example, a type based on age, such as an adult, a child, or an elderly person, sex, or a type based on the seat of the passenger can be given.

[1-2. Process]

[1-2-1. Evacuation Control Process]

Figure 3:
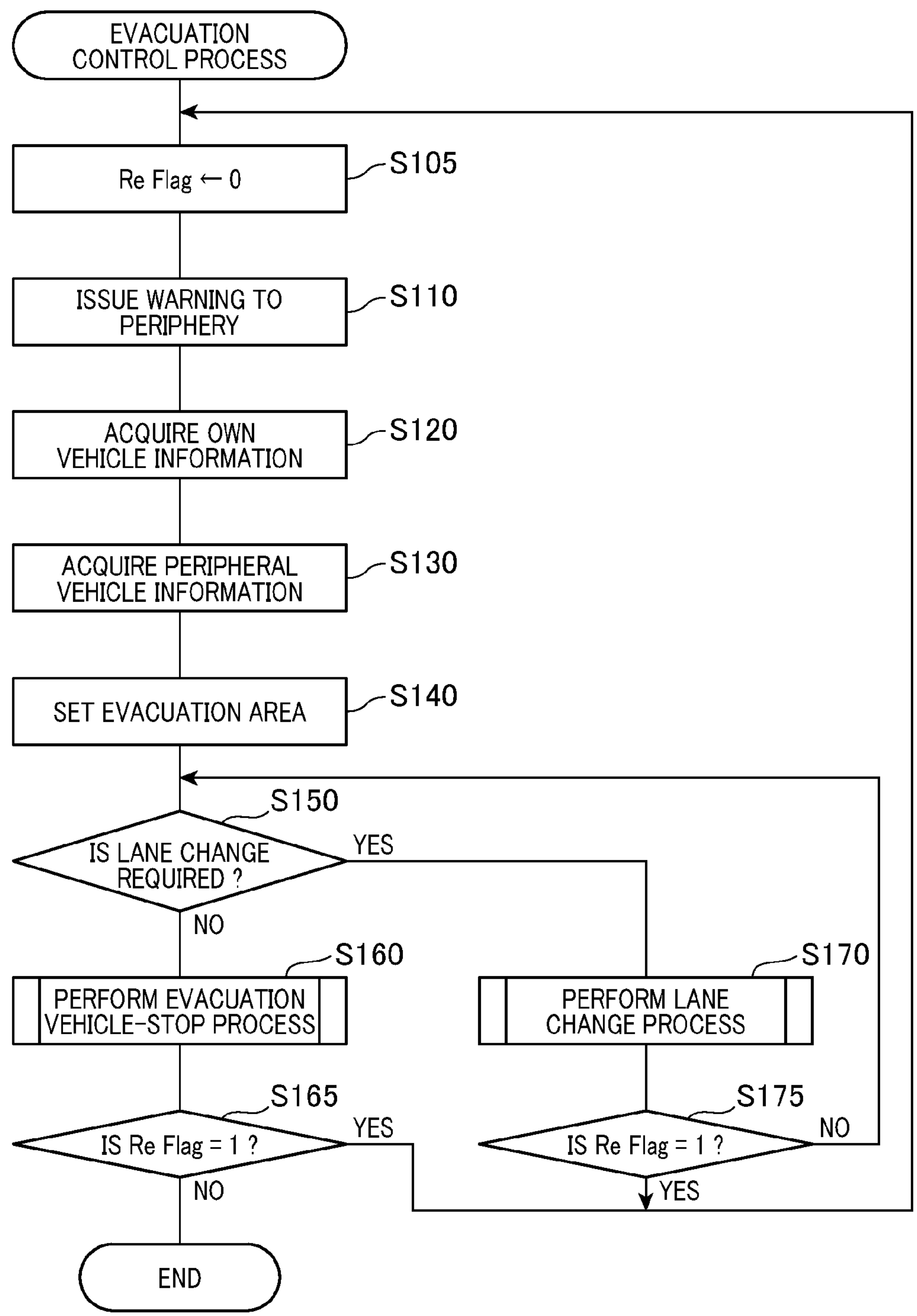
FIG. 3 is a flowchart of an evacuation control process.

Next, the evacuation control process performed by the CPU of the evacuation control apparatus I will be described with reference to the flowchart in FIG. 3. The present process is started when the consciousness level determining unit 11 detects decrease in the consciousness level of the driver. Regarding the decrease in the consciousness level, the consciousness level determining unit 11 determining that the consciousness level of the driver is at the lowest may be considered to be the detection thereof.

When the present process is started, first, at step S105, the evacuation control unit 18 sets a Re Flag, described hereafter, to 0. At subsequent step S110, the warning unit 13 issues a warning to the periphery of the own vehicle. The periphery of the own vehicle herein is merely required to be at least a predetermined area behind the own vehicle. However, according to the present embodiment, the periphery of the own vehicle further includes predetermined areas ahead and to the sides of the own vehicle.

Specifically, the warning unit 13 can notify the periphery of the own vehicle of an emergency situation in which the own vehicle is required to make an emergency stop by wireless communication or operation of the hazard lights, the horn, the brake lamps, the headlights, and the like. Here, when the warning unit 13 issues the warning to the periphery of the own vehicle, the confirming unit 14 outputs confirmation information related to the warning to the evacuation control unit 18. The confirmation information includes, in addition to information indicating whether or not the warning is successful, information indicating either of success level 1 and success level 2 when the warning is successful.

Next, at step S120, the route calculating unit 16 and the evacuation control unit 18 acquire own vehicle information from the vehicle control ECU 12 and the like. For example, the own vehicle information includes information indicating the speed and acceleration, the steering angle, the yaw rate, the current position, and the advancing direction of the own vehicle.

At subsequent step S130, the route calculating unit 16 and the evacuation control unit 18 acquire peripheral vehicle information from the rear monitor sensor 4, the front monitor sensor 6, the navigation system 10, and the like. The peripheral vehicle information includes, as information on the periphery of the own vehicle, the present/absence and positions of peripheral vehicles, and the distinguishing information, distance information, speed information and the like of peripheral vehicles, In addition, the peripheral vehicle information includes the confirmation information inputted from the confirming unit 14 at step S110. When the vehicle information and the peripheral vehicle information are acquired at steps S120 and S130, the route calculating unit 16 sets a plurality of evacuation area candidates based on the acquired vehicle information and peripheral vehicle information. In addition, the route calculating unit 16 generates evacuation target information related to each evacuation area, and outputs the evacuation target information to the evacuation control unit 18.

Then, at step S140, the evacuation control unit 18 sets an evacuation area (such as an evacuation area A shown in FIG. 2) that is the closest to the own vehicle, among evacuation areas that are separated from the current position of the own vehicle by a predetermined safety distance or more, based on the own vehicle information and the peripheral vehicle information acquired at steps S120 and S130, to promptly ensure the safety of the own vehicle, including the driver, and the like. In actuality, an evacuation area that is suitable for the road type, such as the navigation information, is selected. Therefore, in addition to dedicated evacuation areas such as those shown in FIG. 2, a general road-shoulder area, such as an area including a portion of a traffic lane adjacent to the road shoulder, may be selected. However, to avoid complicating the description, a case in which a dedicated evacuation area is selected is mainly described hereafter.

At subsequent step S150, the evacuation control unit 18 determines whether or not a course change of the own vehicle from the current position to the evacuation-area side, such as lane change to the adjacent lane on the road-shoulder side to make the own vehicle perform an emergency evacuation to the evacuation area set at the preceding step S140, is required. According to the present embodiment, the above-described evacuation target information includes the information related to the target traveling route from the own vehicle position to the evacuation area. Therefore, for example, whether or not lane change is required is determined based on this information. According to the present embodiment, when determined that lane change is not required, the evacuation control unit 18 proceeds to step S160. When determined that lane change is required, the evacuation control unit 18 proceeds to step S170.

Then, at step S160, the evacuation control unit 18 performs an evacuation vehicle-stop process, described hereafter. At step S170, the evacuation control unit 18 performs a lane change process, described hereafter. The evacuation vehicle-stop process is a process in which the own vehicle is stopped at the evacuation area without lane change being required. The lane change process is a process in which the own vehicle is made to change traffic lanes to bring the own vehicle closer to the evacuation area.

Finally, at step S165 subsequent to step S160, or at step S175 subsequent to step S170, the evacuation control unit 18 confirms the setting content of the Re Flag that indicates whether or not the present process is required to be repeatedly performed. When the Re Flag is set to 1, which indicates that the present process is required to be repeatedly performed from the beginning, the evacuation control unit 18 returns to step S105. Meanwhile, when the Re Flag is set to 0, which indicates that the present process is not required to be repeatedly performed, at step S165, the evacuation control unit 18 ends the present process. At step S175, the evacuation control unit 18 returns to step S150.

[1-2-2. Evacuation Vehicle-stop Process]

Figure 4:
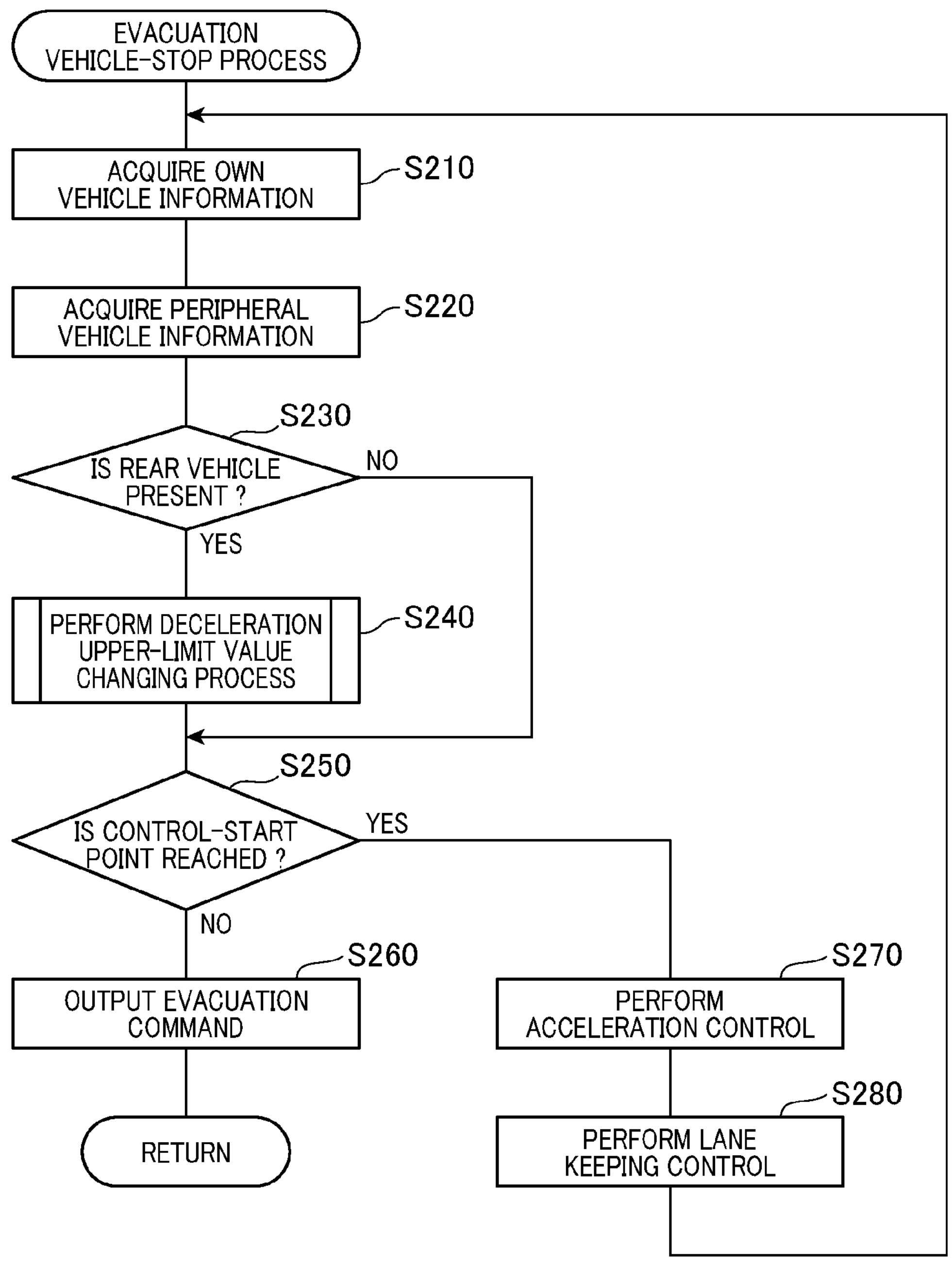
FIG. 4 is a flowchart of an evacuation vehicle-stop process.

Next, the evacuation vehicle-stop process performed by the evacuation control unit 18 at step S160 will be described with reference to the flowchart in FIG. 4.

When the present process is started, first, at step S210, the evacuation control unit 18 acquires the own vehicle information. At subsequent step S220, the evacuation control unit 18 acquires the peripheral vehicle information. The own vehicle information and the peripheral vehicle information are as described earlier.

Next, at step S230, the evacuation control unit 18 determines whether or not a following vehicle is present based on the information acquired from the rear monitor sensor 4. Specifically, the evacuation control unit 18 references the distinguishing information and the like of the rear vehicles based on the target traveling route of the evacuation target information, and determines whether or not a following vehicle (such as the rear vehicle $\alpha$ shown in FIG. 2) is present. When determined that a following vehicle is present, the evacuation control unit 18 proceeds to step S240. When determined that a following vehicle is not present, the evacuation control unit 18 skips to step S250. The determination herein is not limited to the following vehicle. Branching to a step to which the evacuation control unit 18 proceeds based on whether or not a rear vehicle is present is also possible.

At step S240, the evacuation control unit 18 performs a process (hereafter, a deceleration upper-limit value changing process) to change an upper-limit value (hereafter, a deceleration upper-limit value) that prescribes a range of deceleration of the own vehicle that is allowed when the own vehicle is stopped. Deceleration is a decreasing change rate of the vehicle speed. When a comparison is made in a case in which the base point is the same vehicle speed, the stop timing of the own vehicle becomes earlier as the value of the deceleration increases. The stop timing of the own vehicle becomes delayed as the value of the deceleration decreases, The deceleration upper-limit value is a threshold that indicates an upper limit related to deceleration. A distance (that is, a stop distance shown in FIG. 5) until the own vehicle stops can be shortened as the deceleration upper-limit value increases. Therefore, because the stop timing of the own vehicle can be made earlier as the deceleration upper-limit value increases, the own vehicle can be made to perform an emergency evacuation to a closer evacuation area. When a following vehicle is not present, for example, the deceleration upper-limit value is set to a maximum possible deceleration based on the specifications of the own vehicle, as a predetermined maximum upper-limit value, without being changed. Conversely, when a following vehicle is present, the deceleration upper-limit value is set to a value that is less than the maximum upper limit value.

At above-described step S140, the stop distance (hereafter, an upper-limit stop distance) corresponding to the deceleration upper-limit value set in this manner is compared to a distance from the own vehicle to the closest evacuation area A. Specifically, the evacuation control unit 18 determines whether or not the longest evacuation distance is greater than the upper-limit stop distance based on the evacuation target information received from the route calculating unit 16. In this way, when the longest evacuation distance is greater than the upper-limit stop distance, it can be considered that the own vehicle can be made to perform an emergency evacuation to the evacuation area A that is closest to the own vehicle, and the evacuation area can be set.

Meanwhile, when determined that the longest evacuation distance is equal to or less than the upper-limit stop distance, it is considered that the own vehicle cannot be made to perform an emergency evacuation to the evacuation area A. Then, at above-described step S140, for example, the evacuation control unit 18 replaces the evacuation area A with an evacuation area B shown in FIG. 2 that is the next closest evacuation area to the own vehicle. In this way, the evacuation area B can also be set based on the evacuation target information received from the route calculating unit 16. The deceleration upper-limit value changing process will be described hereafter.

Next, at step S250, the evacuation control unit 18 determines whether or not the own vehicle has reached a point (hereafter, a control-start point) that is before the set evacuation area by the above-described safety distance. When the own vehicle has reached the control-start point, the evacuation control unit 18 proceeds to step S260. When the own vehicle has not reached the control-start point, the evacuation control unit 18 proceeds to step S270. The safety distance can be set in advance by a predetermined distance being added to the upper-limit stop distance.

At step S260, the evacuation control unit 18 transmits, to the vehicle control ECU 12 via the in-vehicle LAN 8, control information including a command (hereafter, an evacuation command) related to the set evacuation area. The evacuation command is a command based on the deceleration upper-limit value, as described above. For example, the evacuation command includes the target traveling route to a longest evacuation position of the evacuation area. As a result of the vehicle control ECU 12 receiving the command, vehicle-stop control is performed to make the own vehicle perform an emergency evacuation to the target stop position along the target traveling route, while the own vehicle decelerates at a deceleration equal to or lower than the deceleration upper-limit value. The target stop position is a position within the area prescribed as the evacuation area. For example, a position closest to the own vehicle within a. range in which the own vehicle is able to stop at a deceleration that is equal to or lower than the deceleration upper-limit value is selected as the target stop position.

At step S270, the evacuation control unit 18 transmits, to the vehicle control ECU 12 via the in-vehicle LAN 8, a command related to acceleration control of the own vehicle using ACC, for example, to maintain traveling of the oven vehicle until the own vehicle reaches the control-start point. In addition, at subsequent step S280, the evacuation control unit 18 transmits, to the vehicle control ECU 12 via the in-vehicle LAN 8, a command related to lane keeping control of the own vehicle using LKA, for example, to maintain traveling in the same traveling lane until the own vehicle reaches the control-start point. The evacuation control unit 18 then returns to step S210. [1-2-3. Lane Change Process]

Next, the lane change process performed by the evacuation control unit 18 at step S170 will be described with reference to the flowchart in FIG. 6.

When the present process is started, first, at step S310, the evacuation control unit 18 acquires the own vehicle information. At subsequent step S320, the evacuation control unit 18 acquires the peripheral vehicle information. The own vehicle information and the peripheral vehicle information are as described earlier.

Next, at step S330, the evacuation control unit 18 determines whether or not a peripheral vehicle is present based on the information received from the rear monitor sensor 4 and the front monitor sensor 6. When determined that a peripheral vehicle is present, the evacuation control unit 18 proceeds to step S340. When determined that a peripheral vehicle is not present, the procedure is skipped to step S390. At step S390, the evacuation control unit 18 transmits, to the vehicle control ECU 12 via the in-vehicle LAN 8, control information including a course-change timing command. The course-change timing command is a command related to the course-change timing of the own vehicle. According to the present embodiment, a timing at which the own vehicle changes traffic lanes to the adjacent lane on the evacuation-area side identified as the course-change destination is prescribed.

At step S340, the evacuation control unit 18 performs the deceleration upper-limit value changing process to change the deceleration upper-limit value that is allowed when the own vehicle is decelerated, in relation to a following vehicle in the own lane in which the own vehicle is currently traveling or the rear vehicle $\alpha$ in the adjacent lane on the evacuation-area side. When determined that the rear vehicle is not present at step S330, the evacuation control unit 18 omits this step and skips to step S350.

At subsequent step S350, the evacuation control unit 18 performs an inter-vehicle distance lower-limit value changing process in relation to a vehicle (that is, the side vehicle) traveling in a traffic lane (that is, the adjacent lane) on the side to which the own vehicle is to change traffic lanes, when the own vehicle is to change course (that is, change traffic lanes) to the adjacent lane on the evacuation-area side. The inter-vehicle distance lower-limit value changing process is a process to change a lower-limit value (hereafter, an inter-vehicle distance lower-limit value) that prescribes a range of the inter-vehicle distance that is allowed when the own vehicle changes traffic lanes. When determined that the side vehicle is not present at step S330, the evacuation control unit 18 omits this step and skips to step S370.

The inter-vehicle distance herein refers to the distance between the own vehicle and the side vehicle. Specifically, the inter-vehicle distance is the distance to the side vehicle that is traveling in the adjacent lane that is the lane change destination, in a scenario in which the own vehicle is required to perform lane change. For example, the inter-vehicle distance may be a straight-line distance from the own vehicle to the side vehicle or may be a distance along the traveling lane direction of the own vehicle or the side vehicle. As described earlier, among the other vehicles present in the periphery of the own vehicle, the side vehicle is the vehicle traveling in the traffic lane on the side to which the own vehicle is to change traffic lanes. According to the present embodiment, the inter-vehicle distance is measured for both a side vehicle ahead of the own vehicle (hereafter, a front side vehicle) and a side vehicle behind the own vehicle (hereafter, a rear side vehicle).

The inter-vehicle distance lower-limit value is a threshold that indicates a lower limit related to the inter-vehicle distance. For example, the inter-vehicle distance lower-limit value is set to a large value based on an approaching speed of the side vehicle shown in FIG. 7. Specifically, the inter-vehicle distance lower-limit value is set such that the value thereof increases as the speed at which the side vehicle approaches the own vehicle increases, such as when the speed of the rear side vehicle is high or when the speed of the front side vehicle is low in relation to the speed of the own vehicle. In addition, the inter-vehicle distance lower-limit value may be set such that the value thereof increases as the speed at which the side vehicle moves away from the own vehicle decreases. A relational expression of the inter-vehicle distance lower-limit value and the relative speed may be linear or may be non-linear. In addition, the relational expression may differ between that for the front side vehicle and that for the rear side vehicle, or may be the same. The inter-vehicle speed lower-limit changing process will be described hereafter.

The inter-vehicle distance lower-limit value set in this manner is compared to the inter-vehicle distance at the next step. Specifically, at subsequent step S360, the evacuation control unit 18 sets the inter-vehicle distance lower-limit value based on the speed information received from the rear monitor sensor 4 and the front monitor sensor 6. The evacuation control unit 18 then determines whether or not the inter-vehicle distance between the own vehicle and the side vehicle is equal to or less than the set inter-vehicle distance lower-limit value based on the distance information. When determined that the inter-vehicle distance falls below than the inter-vehicle distance lower-limit value, the evacuation control unit 18 proceeds to step S400. When the inter-vehicle distance falls below the inter-vehicle distance lower-limit value, the evacuation control unit 18 may wait until the inter-vehicle distance becomes equal to or greater than the inter-vehicle distance lower-limit value. This wait time has a tendency to become shorter as the inter-vehicle distance lower-limit value decreases. In addition, the course-change timing becomes earlier as the wait time becomes shorter. Therefore, in this case, the course-change timing tends to become earlier as the inter-vehicle distance lower-limit value decreases.

When determined that the inter-vehicle distance is equal to or greater than the inter-vehicle distance lower-limit value, at step S370, the warning unit 13 notifies the periphery that the own vehicle is changing traffic lanes. Specifically, the warning unit 13 gives notification that the own vehicle is changing traffic lanes to the adjacent lane on the evacuation-area side by operating a turn signal. Furthermore, the warning unit 13 may also notify the periphery of the oven vehicle by wireless communication, or by operating the hazard lights, the brake lamps, the horn, the headlights, and the like.

At subsequent step S380, the evacuation control unit 18 transmits, to the vehicle control ECU 12 via the in-vehicle LAN 8, a command related to acceleration control of the own vehicle using, for example, ACC. Then, at step S390, the evacuation control unit 18 makes the vehicle control ECU 12 perform lane change control by transmitting, to the vehicle control ECU 12 via the in-vehicle LAN 8, control information including the course-change timing command. The evacuation control unit 18 then ends the present process. The course-change timing command is as described earlier. As a result of the vehicle control ECU 12 receiving this command, the lane change of the own vehicle is performed. The order in which the steps of steps S380 and S390 are performed may be interchanged.

Meanwhile, at step S400, the evacuation control unit 18 transmits, to the vehicle control ECU 12 via the in-vehicle LAN 8, a command related to acceleration control of the vehicle using, for example, ACC to maintain traveling of the own vehicle until the own vehicle reaches the control-start point. In addition, at subsequent step S410, the evacuation control unit 18 transmits, to the vehicle control ECU 12 via the in-vehicle LAN 8, a command related to lane keeping control of the vehicle using, for example, LKA to maintain traveling of the own vehicle in the same traveling lane.

Then, at step S420, the evacuation control unit 18 determines whether or not the own vehicle has reached the control-start point at step S140. When the own vehicle has reached the control-start point, the evacuation control unit 18 proceeds to step S425. The evacuation control unit 18 sets the above-described Re Flag to 1 and ends the present process. Meanwhile, when the own vehicle has not reached the control-start point, the evacuation control unit 18 returns to step S310.

[1-2-4. Inter-vehicle Distance Lower-limit Value Changing Process]

Figure 8:
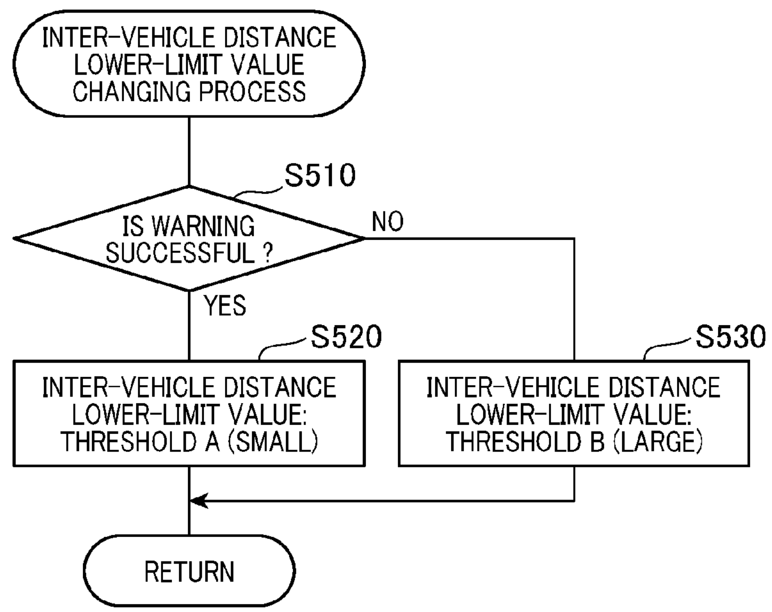
FIG. 8 is a flowchart of an inter-vehicle distance lower-limit value changing process.

Next, the inter-vehicle distance lower-limit value changing process performed by the evacuation control unit 18 at step S350 will be described with reference to the flowchart in FIG. 8. Of the evacuation control unit 18, the configuration of the function related to the present process corresponds to a lower-limit changing unit.

When the present process is started, first at step S510, the evacuation control unit 18 determines whether or not the warning by the warning unit 13 is successful. Specifically, the evacuation control unit 18 determines whether or not the warning is successful based on the confirmation information received from the confirming unit 14 within a predetermined amount of time of reception of the detection information indicating the decrease in the consciousness level of the driver from the consciousness level determining unit 11.

Figure 5:
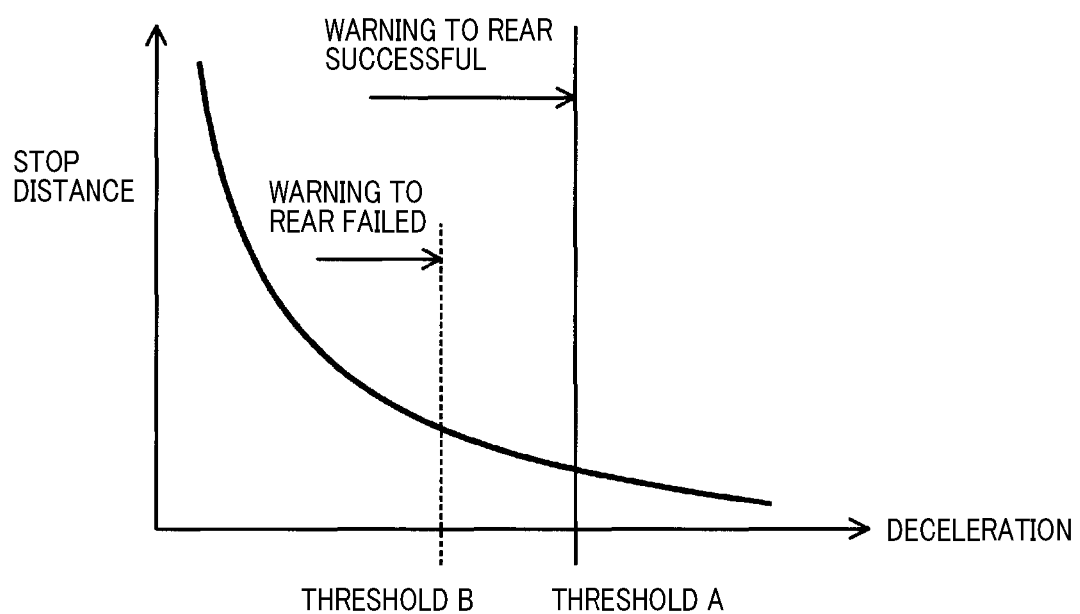
FIG. 5 is an explanatory diagram of a deceleration upper-limit value.

When the success of the warning is confirmed, at step S520, the evacuation control unit 18 sets the relational expression of the inter-vehicle lower-limit value to, for example, a relational expression of a threshold A shown in FIG. 5. When the success of the warning is not confirmed, at step S530, the evacuation control unit 18 sets the relational expression of the inter-vehicle lower-limit value to, for example, a relational expression of a threshold B that is greater than the threshold A shown in FIG. 5.

As described earlier, the course-change timing tends become earlier as the inter-vehicle distance lower-limit value decreases. Therefore, when the warning is successful, the inter-vehicle distance lower-limit value is set to be less than that when the warning is not successful, that is, has failed. As a result, it becomes at least easier to make the course-change timing earlier. In addition, when the warning has failed, the inter-vehicle distance lower-limit value is set to be greater than that when the warning is successful. As a result, it becomes at least easier to delay the course-change timing.

The inter-vehicle distance lower-limit value set in this manner is used to determine the course-change timing of the own vehicle in the lane change process, described earlier.

[1-2-5. Deceleration Upper-limit Value Changing Process]

Figure 9:
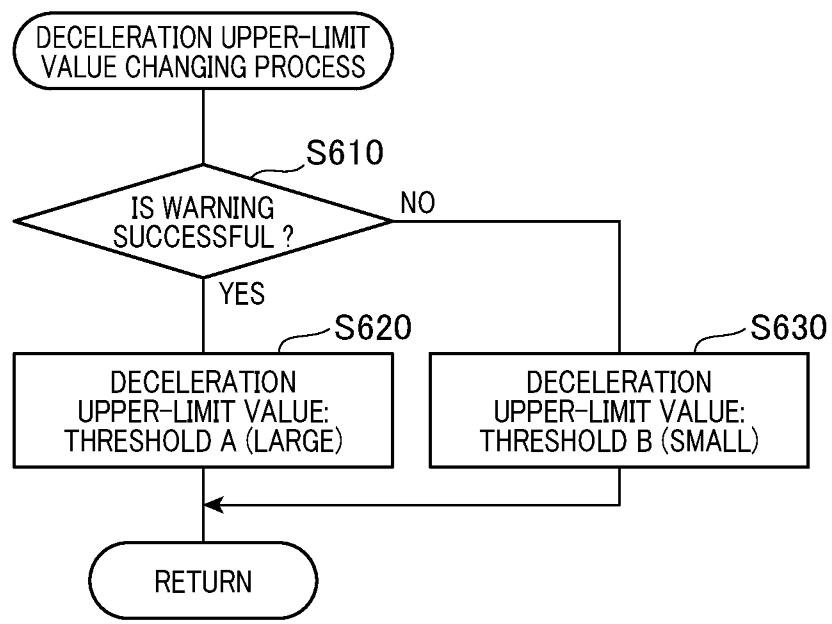
FIG. 9 is a flowchart of a deceleration upper-limit value changing process.

Next, the deceleration upper-limit value changing process performed by the evacuation control unit 18 at steps S240 and S340 will be described with reference to the flowchart in FIG. 9. Of the evacuation control unit 18, the configuration of the function related to the present process corresponds to an upper-limit value changing unit.

When the present process is started, first, at step S610, the evacuation control unit 18 determines whether or not the warning by the warning unit 13 is successful. A specific aspect is similar to that at step S510. When the success of the warning is confirmed, at step S620, for example, the evacuation control unit 18 sets the deceleration upper-limit value to, for example, a threshold A shown in FIG. 7. When the success of the warning is not confirmed, at step S630, the evacuation control unit 18 sets the deceleration upper-limit value to, for example, a threshold B that is less than the threshold A shown in FIG. 7.

As described earlier, the stop timing of the own vehicle can be made earlier as the deceleration upper-limit value increases. Therefore, when the warning is successful, the deceleration upper-limit value is set to be greater than that when the warning is not successful, that is, has failed. As a result, it becomes easier to make the stop timing of the own vehicle earlier. In addition, when the warning has failed, the deceleration upper-limit value is set to be less than that when the warning is successful. As a result, it becomes easier to delay the stop timing of the own vehicle.

The deceleration upper-limit value set in this manner is used to determine the evacuation area of the own vehicle, and further, the stop timing of the own vehicle in the evacuation vehicle-stop process. In addition, the deceleration upper-limit value can also be used to ensure the inter-vehicle distance to the front side vehicle in the lane change process.

[1-3. Variation Examples]

[1-3-1. Inter-vehicle Distance Low-limit Value Changing Process]

Figure 10:
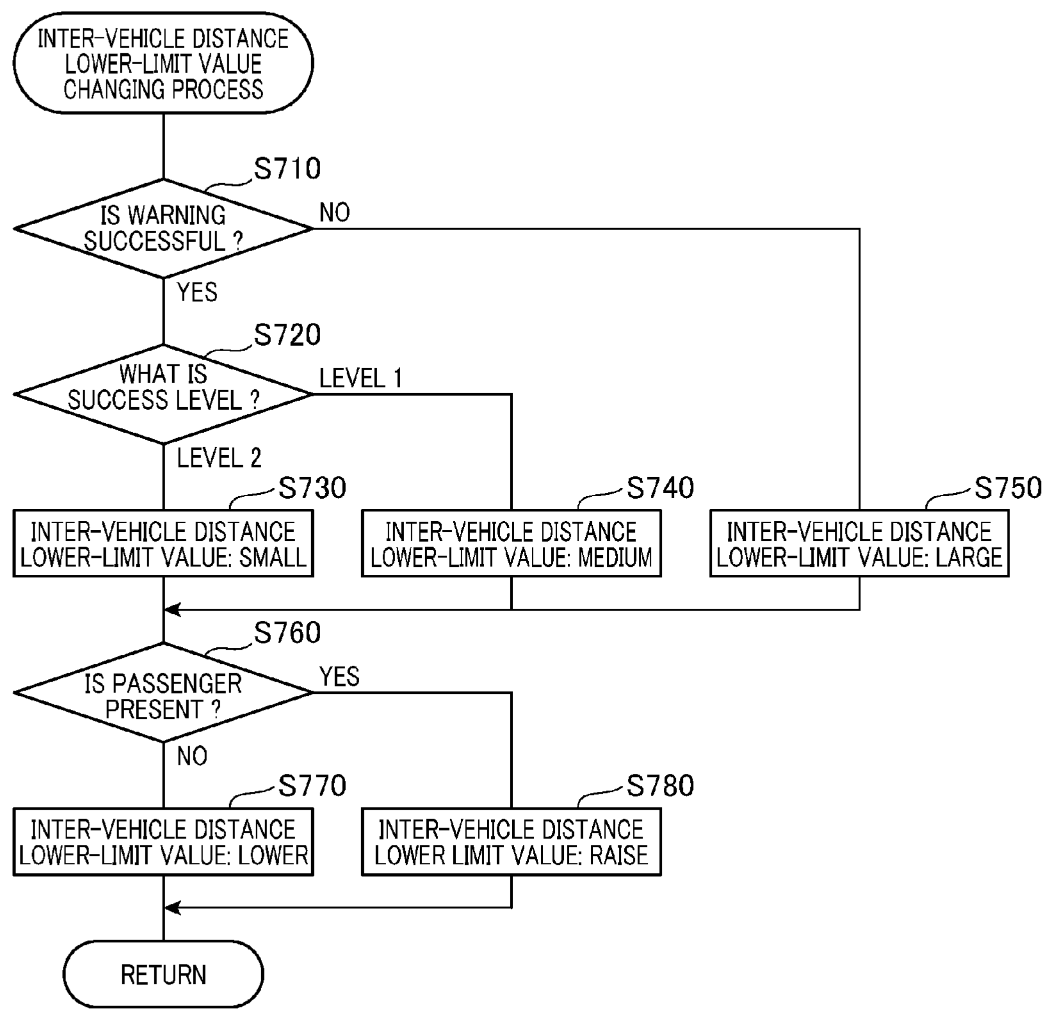
FIG. 10 is a flowchart of a variation example of the inter-vehicle speed lower-limit value changing process.

Next, a variation example of the inter-vehicle distance lower-limit value changing process performed by the evacuation control unit 18 at step S350 will be described with reference to the flowchart in FIG. 10. In the process described earlier, the inter-vehicle distance lower-limit value is variably set based on whether or not the warning is successful.

In this regard, in the present variation example, the process differs from the process described earlier in that, when the warning is successful, the inter-vehicle distance lower-limit value is variably set also based on the success level of the warning. In addition, in the present variation example, the process differs from the process described earlier in that the inter-vehicle distance lower-limit value is changed also based on whether or not a passenger is present, in the present variation example, the basic steps are similar to those of the process described earlier. Therefore, descriptions of common steps are omitted. The differences are mainly described.

When the present process is started, first, at step S710, the evacuation control unit 18 determines whether or not the warning by the warning unit 13 is successful. When the success of the warning is confirmed, the evacuation control unit 18 proceeds to step S720. When the success of the warning is not confirmed, at step S750, the evacuation control unit 18 sets the relational expression of the inter-vehicle lower-limit value to, for example, the relational expression of the threshold B that is greater than the threshold A shown in FIG. 7.

At step S720, the evacuation control unit 18 determines the success level of the warning based on the confirmation information inputted from the confirming unit 14. Specifically, when the information indicating the success level 1 is included in the confirmation information, the evacuation control unit 18 proceeds to step S740. When the information indicating the success level 2 is included in the confirmation information, the evacuation control unit 18 proceeds to step S730.

Figure 7:
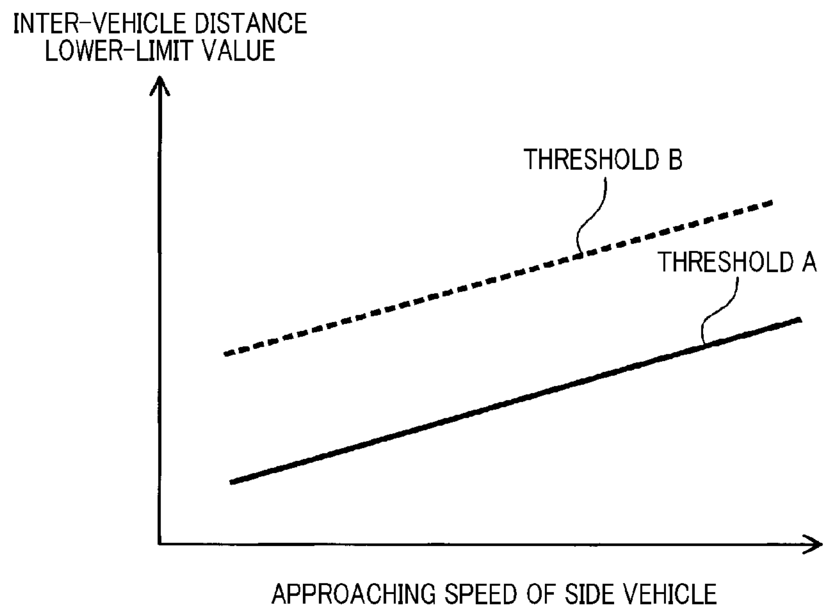
FIG. 7 is an explanatory diagram of an inter-vehicle distance lower-limit value.

At step S730, the evacuation control unit 18 sets the relational expression of the inter-vehicle lower-limit value to, for example, the relational expression of the threshold A that is less than the threshold B shown in FIG. 7. Meanwhile, at step S740, the evacuation control unit 18 sets the relational expression of the inter-vehicle lower-limit value to, for example, the relational expression of a threshold that is less than the threshold B and greater than the threshold A shown in FIG. 7.

As described earlier, the course-change timing tends become earlier as the inter-vehicle distance lower-limit value decreases. Therefore, in cases in which the warning is successful, when the success at the second level is confirmed, the inter-vehicle distance lower-limit value is set to be less than that when the success at the second level is not confirmed, that is, when the success at only the first level is confirmed. As a result, it becomes easier to make the course-change timing earlier. In addition, when the success at only the first level is confirmed, the inter-vehicle distance lower-limit value is set to be greater than that when the success at the second level is confirmed. As a result, it becomes easier to delay the course-change timing. Furthermore, when the warning has failed, the inter-vehicle distance lower-limit value is set to be greater than that when the warning is successful. As a result, it becomes further easier to delay the course-change timing. In this manner, in the present variation example, the course changing timing is adjusted by the inter-vehicle distance lower-limit value being variably changed based on the success level of the warning, in addition to whether or not the warning is successful.

Next, at step S760, the evacuation control unit 18 determines whether or not a passenger is present in the own vehicle based on the detection result from the passenger detecting unit 19. When determined that a passenger is not present, the evacuation control unit 18 proceeds to step S770. When determined that a passenger is present, at step S780, regarding the relational expression of the inter-vehicle distance lower-limit value set at any of steps S730 to S750, the evacuation control unit 18 raises the relational expression of the set value such that the inter-vehicle distance lower-limit value becomes greater.

Meanwhile, at step S770, regarding the relational expression of the inter-vehicle distance lower-limit value set at any of steps S730 to S750, the evacuation control unit 18 lowers the relational expression of the set value such that the inter-vehicle distance lower-limit value becomes smaller.

As described earlier, the course-change timing tends become earlier as the inter-vehicle distance lower-limit value decreases. Meanwhile, lane change in a state in which the inter-vehicle distance to the side vehicle is short can be more easily performed as the inter-vehicle distance lower-limit value decreases. Therefore, when a passenger is not present in the own vehicle, the inter-vehicle distance lower-limit value is set to be less than that when a passenger is present. As a result, it becomes easier to make the course-change timing earlier. In addition, when a passenger is present in the own vehicle, the inter-vehicle distance lower-limit value is set to be greater than that when a passenger is not present. As a result, it becomes more difficult for lane change of the own vehicle to be performed in a state in which the inter-vehicle distance to a side vehicle, particularly a front side vehicle, is short.

In the present variation example, the inter-vehicle distance lower-limit value may also be changed based on the type of passenger. For example, when the passenger is a child, an elderly person, or the like, the inter-vehicle distance lower-limit value may be set to be greater than that when the passenger is an adult. When the seat of the passenger is the passenger seat, the inter-vehicle distance lower-limit value may be set to be greater than that when the seat of the passenger is the backseat. In addition, the inter-vehicle distance lower-limit value may also be changed based on the degree of the consciousness level of the driver.

[1-3-2. Deceleration Upper-limit Value Changing Process]

Figure 11:
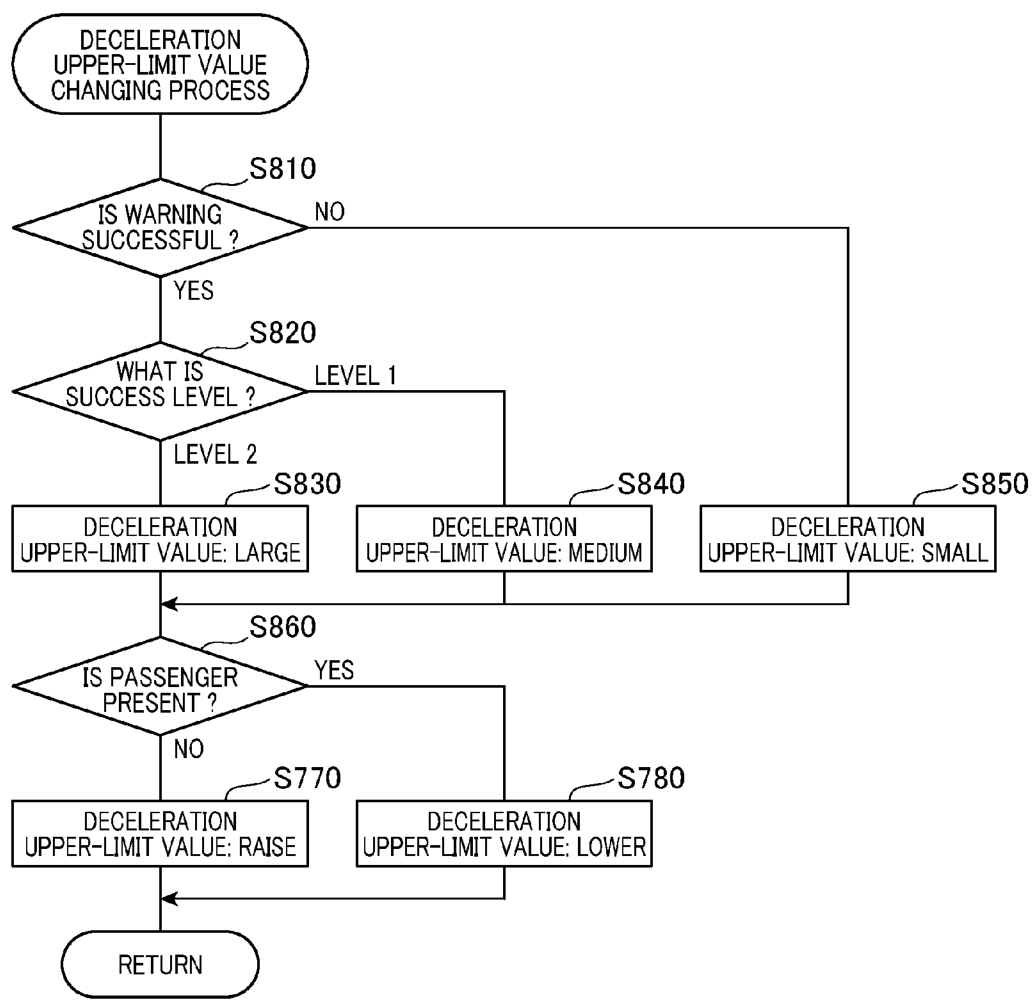
FIG. 11 is a flowchart of a variation example of the deceleration upper-limit value changing process.

Next, a variation example of the deceleration upper-limit value changing process performed by the evacuation control unit 18 at steps S240 and S340 will be described with reference to the flowchart in FIG. 11. In the process described earlier, the deceleration upper-limit value is variably set based on whether or not the warning is successful. In this regard, in the present variation example, the process differs from the process described earlier in that, when the warning is successful, the deceleration upper-limit value is variably set also based on the success level of the warning. In addition, in the present variation example, the process differs from the process described earlier in that the deceleration upper-limit value is changed also based on whether or not a passenger is present. In the present variation example, the basic steps are similar to those of the process described earlier. Therefore, descriptions of common steps are omitted. The differences are mainly described.

When the present process is started, first, at step S810, the evacuation control unit 18 determines whether or not the warning by the warning unit 13 is successful. When the success of the warning is confirmed, the evacuation control unit 18 proceeds to step S820. When the success of the warning is not confirmed, at step S850, the evacuation control unit 18 sets the deceleration upper-limit value to, for example, the threshold B that is less than the threshold A shown in FIG. 5.

At step S820, the evacuation control unit 18 determines the success level of the warning based on the confirmation information inputted from the confirming unit 14. Specifically, when the information indicating the success level 1 is included in the confirmation information, the evacuation control unit 18 proceeds to step S840. When the information indicating the success level 2 is included in the confirmation information, the evacuation control unit 18 proceeds to step S830.

At step S830, the evacuation control unit 18 sets the deceleration upper-limit value to, for example, the threshold A that is less than the threshold B shown in FIG. 5. Meanwhile, at step S840, the evacuation control unit 18 sets the deceleration upper-limit value to, for example, a threshold that is greater than the threshold B and less than the threshold A shown in FIG. 5.

As described earlier, the stop timing of the own vehicle can be made earlier as the deceleration upper-limit value increases. Therefore, in cases in which the warning is successful, when the success at the second level is confirmed, the deceleration upper-limit value is set to be greater than that when the success at the second level is not confirmed, that is, when the success at only the first level is confirmed. As a result, it becomes easier to make the stop timing of the own vehicle earlier. In addition, when the success at only the first level is confirmed, the deceleration upper-limit value is set to be less than that when the success at the second level is confirmed. As a result, it becomes easier to delay the stop timing of the own vehicle. Furthermore, when the warning has failed, the deceleration upper-limit value is set to be less than that when the warning is successful. As a result, it becomes further easier to delay the stop timing of the own vehicle. In this way, in the present variation example, the stop timing of the own vehicle is adjusted by the deceleration upper-limit value being variably set based on the success level of the warning, in addition to whether or not the warning is successful.

Next, at step S860, the evacuation control unit 18 determines whether or not a passenger is present in the own vehicle based on the detection result from the passenger detecting unit 19. When determined that a passenger is not present, the evacuation control unit 18 proceeds to step S870. When determined that a passenger is present, at step S880, the evacuation control unit 18 lowers the deceleration upper-limit value set at any of steps S830 to S850.

Meanwhile, at step S870, the evacuation control unit 18 raises the deceleration upper-limit value set at any of steps S830 to S850. As described earlier, the stop timing of the own vehicle can be made earlier as the deceleration upper-limit value increases. Meanwhile, sudden braking of the own vehicle tends to be performed when the deceleration upper-limit value increases. Therefore, when a passenger is not present in the own vehicle, the deceleration upper-limit value is set to be greater than that when a passenger is not present. As a result, it becomes easier to make the stop timing of the own vehicle earlier. In addition, when a passenger is present in the own vehicle, the deceleration upper-limit value is set to be less than when a passenger is not present. As a result, it becomes more difficult for the sudden braking of the own vehicle to be performed.

In the present variation example, the deceleration upper-limit value may also be changed based on the type of passenger. For example, when the passenger is a child, an elderly person, or the like, the deceleration upper-limit value may be set to be less than that when the passenger is an adult. When the seat of the passenger is the passenger seat, the deceleration upper-limit value may be set to be less than that when the seat of the passenger is the backseat. In addition, the deceleration upper-limit value may also be changed based on the degree of the consciousness level of the driver.

[1-4. Effects]

According to the first embodiment, described in detail above, the following effects are achieved.

(1a) When the own vehicle is to perform an emergency evacuation, traveling assistance control that takes into consideration rear monitor results becomes possible. Therefore, deceleration, course change, and the like based on the state behind the own vehicle can be performed. As a result, care for a following vehicle and promptness of evacuation can both be achieved.

(2a) In addition, traveling assistance control that takes into consideration warning confirmation results becomes possible. Therefore, deceleration, course change, and the like based on whether or not the warning to the rear of the own vehicle is successful can be performed. As a result of this as well, care for a following vehicle and promptness of evacuation can both be achieved.

(3a) Specifically, for example, based on whether or not a following vehicle is present, when a following vehicle is not present in the own lane, the deceleration upper-limit value is set to the predetermined maximum upper-limit value, without being changed. Therefore, the own vehicle can be stopped with maximum promptness.

(4a) In addition, for example, when a following vehicle is present in the own lane, the deceleration upper-limit value is changed to a value that is less than the maximum upper-limit value. Therefore, the stop timing can be delayed from that when the following vehicle is not present. Furthermore, at least the inconvenience inflicted on the driver of the following vehicle can he suppressed.

(5a) In addition, for example, when a following vehicle is present in the own lane, the deceleration upper-limit value is changed to that based on whether or not the warning to the rear of the own vehicle is successful. Therefore, a differing deceleration mode can be applied based on whether or not the state is such that the driver of the following vehicle can easily prepare in advance. As a result of this as well, care for a following vehicle and promptness of evacuation can both be achieved.

(6a) Specifically, for example, when the warning is successful, the deceleration upper-limit value is set to be greater than that when the warning is not successful. Therefore, when the state is such that the driver of the following vehicle can easily prepare in advance, the stop timing can be made earlier than that in a state in which advanced preparation is difficult. The own vehicle can be promptly stopped upon appropriately seeking cooperation from the following vehicle.

(7a) In addition, for example, based on whether or not a rear vehicle is present, when a rear vehicle (that is, a side vehicle) is not present in an adjacent lane on the road-shoulder side, the course-change timing to the road-shoulder side is not changed. Therefore, the own vehicle can change courses with maximum promptness.

(8a) In addition, for example, when a side vehicle is present in the adjacent lane on the road-shoulder side, the course-change timing is changed. Therefore, the course-change timing can be delayed from that when a side vehicle is not present. Furthermore, at least inconvenience inflicted on the driver of the side vehicle can be suppressed.

(9a) In addition, for example, when a side vehicle is present in the adjacent lane on the road-shoulder side, the course-change timing is changed to that based on whether or not the warning to the periphery of the own vehicle is successful. Therefore, a differing course change can be applied based on whether or not the state is such that the driver of the side vehicle can easily prepare in advance. As a result of this as well, care for a side vehicle and promptness of evacuation can both be achieved.

(10a) Specifically, for example, when the warning is successful, the course-change timing is set to be at least more easily earlier than that when the warning is not successful. As a result, when the state is such that the driver of the side vehicle can easily prepare in advance, the course-change timing can be made earlier than that in a state in which advanced preparation is difficult. The own vehicle can promptly change courses upon appropriately seeking cooperation from the side vehicle.

(11a) In addition, specifically, for example, based on whether or not a following vehicle is present, when a following vehicle (that is, a side vehicle) is not present in an adjacent lane on the road-shoulder side or the like, the inter-vehicle distance lower-limit value is not changed. Therefore, the own vehicle can change traffic lanes with maximum promptness.

(12a) In addition, for example, when a side vehicle is present in the adjacent lane on the road-shoulder side, the inter-vehicle distance lower-limit value is changed. Therefore, the lane-change timing can be delayed from that when a side vehicle is not present. Furthermore, at least inconvenience inflicted on the driver of the following vehicle can be suppressed.

(13a) Specifically, for example, when the warning is successful, the inter-vehicle distance lower-limit value is set to be less than that when the warning is not successful. Therefore, when the state is such that the driver of the side vehicle can easily prepare in advance, the stop timing can be made earlier than that in a state in which advanced preparation is difficult. The own vehicle can promptly change courses upon appropriately seeking cooperation from the side vehicle.

(14a) In addition, the deceleration upper-limit value and the inter-vehicle lower-limit value are changed based on the success level of the warning. Therefore, for example, when the probability of obtaining the cooperation of a peripheral vehicle is high, the stop timing or the lane-change timing of the own vehicle can be made further earlier. The promptness of an emergency stop of the own vehicle can be further ensured.

(15a) In addition, the success level of the warning is raised when a response from a peripheral vehicle in relation to the warning is detected. As a result, the probability of obtaining the cooperation of a peripheral vehicle can be favorably estimated.

(16a) In addition, the response from a peripheral vehicle in relation to the warning is also detected from changes in the behavior of the peripheral vehicle. As a result, for example, the response from a peripheral vehicle can be detected without inter-vehicle communication being performed. Furthermore, the response from a peripheral vehicle can be detected without communication apparatuses being provided in the own vehicle and other vehicles.

(17a) in addition, the deceleration upper-limit value and the inter-vehicle distance lower-limit value are changed based on whether or not a passenger is present in the own vehicle. Therefore, when a passenger is not present, the stop timing or the lane-change timing of the own vehicle can be made further earlier. The promptness of an emergency stop of the own vehicle can be further ensured. Meanwhile, when a passenger is present, avoidance of sudden braking and lane change with sufficient inter-vehicle distance to a side vehicle can be performed. Burden placed on the passenger can be further reduced.

[2. Other Embodiments]

An embodiment of the present invention is described above. However, the present invention is not limited to the above-described embodiment. Various modes are possible.

(2a) According to the above-described embodiment, at S350 to S360, the course-change timing is adjusted by the inter-vehicle distance lower-limit value being variably set based on whether or not the warning to the periphery of the own vehicle is successful. However, the present invention is not limited thereto. For example, the wait time related to the course-change timing may be variably set based on whether or not the warning to the periphery of the own vehicle is successful. Specifically, the wait time may be shortened when the warning is successful, and the wait time may be lengthened when the warning has failed. The course-change timing command may be outputted when the wait time has elapsed.

(2b) A function provided by a single constituent element according to the above-described embodiment may be distributed as a plurality of constituent elements. Functions provided by a plurality of constituent elements may be integrated into a single constituent element. In addition, at least a part of a configuration according to the above-described embodiment may be replaced by a publicly known configuration providing similar functions. Furthermore, a part of a configuration according to the above-described embodiment may be omitted. Moreover, at least a part of a configuration according to an above-described embodiment may be added to or replace a configuration according to another above-described embodiment. All aspects included in the technical concept identified solely by the expressions recited in the scope of claims are embodiments of the present invention.

(2c) The present invention can also be actualized by various modes in addition to the above-described evacuation control apparatus 1, such as a system of which a constituent element is the evacuation control apparatus 1, a single or a plurality of programs enabling a computer to function as the evacuation control apparatus 1, a single or a plurality of non-transitory, tangible recording media, such as a semiconductor memory, on which at least a part of the program is recorded, and an evacuation control method.

The invention claimed is:

1. An evacuation control apparatus comprising a decrease detecting unit that detects, using a processor, a decrease in a consciousness level of a driver of an own vehicle;

a rear monitoring unit that monitors, using the processor, a state behind the own vehicle;

an evacuation control unit that outputs, using the processor, control information for making the own vehicle perform an emergency evacuation based on monitoring results from the rear monitoring unit, in response to the decrease detecting unit detecting a decrease in the consciousness level of the driver, the evacuation control unit including an upper-limit value changing unit that changes a deceleration upper-limit value in response to another vehicle being present behind the own vehicle, the deceleration upper-limit value comprising a range of deceleration of the own vehicle that is allowed in response to the own vehicle being stopped;

a warning unit that issues, using the processor, a warning to the rear of the own vehicle in response to the decrease detecting unit detecting a decrease in the consciousness level of the driver; and a confirming unit that confirms, using the processor, whether the warning by the warning unit is successful, wherein the upper-limit value changing unit changes the deceleration upper-limit value based on confirmation results from the confirming unit in response to another vehicle being present behind the own vehicle.

2. The evacuation control apparatus according to claim 1, wherein:

the upper-limit value changing unit sets, in response to the warning being successful, the deceleration upper-limit value to be greater than that in response to the warning not being successful.

3. The evacuation control apparatus according to claim 2, wherein:

the upper-limit value changing unit sets, with a vehicle traveling in a same traffic lane as the own vehicle, among other vehicles present behind the own vehicle, as a following vehicle, in response to the warning being successful and a response from the following vehicle in relation to the warning being detected, the deceleration upper-limit value to be greater than that in response to the response not being detected.

4. The evacuation control apparatus according to claim 3, wherein:

the upper-limit value changing unit detects the response based on behavior of the following vehicle.

5. The evacuation control apparatus according to claim 4, further comprising:

a passenger detecting unit that detects, using the processor, presence or absence of a passenger in the own vehicle, wherein the upper-limit value changing unit sets, in response to the passenger not being present in the own vehicle based on detection results from the passenger detecting unit, the deceleration upper-limit value to be greater than that in response to the passenger being present.

6. The evacuation control apparatus according to claim 5, further comprising:

a front monitoring unit that monitors, using the processor, a state ahead of the own vehicle, wherein the evacuation control unit outputs the control information based on monitoring results from at least either of the rear monitoring unit and the front monitoring unit.

7. The evacuation control apparatus according to claim 6, wherein:

the evacuation control unit includes a lower-limit value changing unit that, with a vehicle traveling in a traffic lane on a side to which the own vehicle is to change traffic lanes, among other vehicles present in the periphery of the own vehicle, as a side vehicle, and with a lower limit value prescribing a range of an inter-vehicle distance to the side vehicle that is allowed in response to the own vehicle being configured to change traffic lanes as an inter-vehicle distance lower limit value, in response to the side vehicle being present in the periphery of the own vehicle, changes the inter-vehicle distance lower-limit value.

8. The evacuation control apparatus according to claim 7, wherein:

the warning unit issues a warning to the periphery of the own vehicle in response to the decrease detecting unit detecting a decrease in the consciousness level of the driver;

the confirming unit confirms whether the warning to the periphery of the own vehicle by the warning unit is successful; and the lower-limit value changing unit changes the inter-vehicle distance lower-limit value based on confirmation results from the confirming unit in response to the side vehicle being present in the periphery of the own vehicle.

9. The evacuation control apparatus according to claim 8, wherein:

the lower-limit value changing unit sets, in response to the warning being successful, the inter-vehicle distance lower-limit value to be less than that in response to the warning not being successful.

10. The evacuation control apparatus according to claim 9, wherein:

the lower-limit value changing unit sets, in response to the warning being successful and a response from the side vehicle in relation to the warning being detected, the inter-vehicle lower-limit value to be less than that when the response is not detected.

11. The evacuation control apparatus according to claim 10, wherein:

the lower-limit value changing unit detects the response based on behavior of the side vehicle.

12. The evacuation control apparatus according to claim 11, wherein:

the lower-limit value changing unit sets, in response to the passenger not being present in the own vehicle based on detection results from the passenger detecting unit, the inter-vehicle distance lower-limit value to be less than that in response to the passenger being present.

13. The evacuation control apparatus according to claim 7, wherein:

the lower-limit value changing unit sets, in response to the passenger not being present in the own vehicle based on detection results from the passenger detecting unit, the inter-vehicle distance lower-limit value to be less than that in response to the passenger being present.

14. The evacuation control apparatus according to claim 1, further comprising:

a front monitoring unit that monitors, using the processor, a state ahead of the own vehicle, wherein the evacuation control unit outputs the control information based on monitoring results from at least either of the rear monitoring unit and the front monitoring unit.

15. An evacuation control method comprising:

detecting, by an evacuation control apparatus mounted in an own vehicle, a decrease in a consciousness level of a driver of the own vehicle;

issuing, by the evacuation control apparatus, a warning to the rear of the own vehicle in response to the decrease in the consciousness level of the driver being detected;

confirming, by the evacuation control apparatus, whether the warning is successful; and outputting, by the evacuation control apparatus, control information for making the own vehicle perform an emergency evacuation.

16. An evacuation control apparatus comprising:

a decrease detecting unit that detects, using a processor, a decrease in a consciousness level of a driver of an own vehicle;

a rear monitoring unit that monitors, using the processor, a state behind the own vehicle;

an evacuation control unit that outputs, using the processor, control information for making the own vehicle perform an emergency evacuation based on monitoring results from the rear monitoring unit, in response to the decrease detecting unit detecting a decrease in the consciousness level of the driver, the evacuation control unit including an upper-limit value changing unit that changes a deceleration upper-limit value in response to another vehicle being present behind the own vehicle, the deceleration upper-limit value comprising a range of deceleration of the own vehicle that is allowed in response to the own vehicle being stopped; and a passenger detecting unit that detects, using the processor, presence or absence of a passenger in the own vehicle, wherein the upper-limit value changing unit sets, in response to the passenger not being present in the own vehicle based on detection results from the passenger detecting unit, the deceleration upper-limit value to be greater than that in response to the passenger being present.

17. An evacuation control apparatus comprising:

a decrease detecting unit that detects, using a processor, a decrease in a consciousness level of a driver of an own vehicle;

a rear monitoring unit that monitors, using the processor, a state behind the own vehicle; and an evacuation control unit that outputs, using the processor, control information for making the own vehicle perform an emergency evacuation based on monitoring results from the rear monitoring unit, in response to the decrease detecting unit detecting a decrease in the consciousness level of the driver, wherein the evacuation control unit includes a lower-limit value changing unit that, with a vehicle traveling in a traffic lane on a side to which the own vehicle is to change traffic lanes, among other vehicles present in the periphery of the own vehicle, as a side vehicle, and with a lower limit value prescribing a range of an inter-vehicle distance to the side vehicle that is allowed in response to the own vehicle being configured to change traffic lanes as an inter-vehicle distance lower limit value, in response to the side vehicle being present in the periphery of the own vehicle, changes the inter-vehicle distance lower-limit value.

* * * * *